United States Patent
Tamai et al.

(10) Patent No.: US 6,835,846 B2
(45) Date of Patent: Dec. 28, 2004

(54) ALIPHATIC COMPOUNDS, PROCESS FOR THEIR PREPARATION AND THEIR USAGE

(75) Inventors: Tadakazu Tamai, Ibaraki (JP); Masazumi Nishikawa, Ibaraki (JP); Kenji Mori, Tokyo (JP)

(73) Assignee: Maruha Corporation, Tokyo (JP)

( * ) Notice: Subject to any disclaimer, the term of this patent is extended or adjusted under 35 U.S.C. 154(b) by 76 days.

(21) Appl. No.: 10/398,921

(22) PCT Filed: Oct. 12, 2001

(86) PCT No.: PCT/JP01/08992

§ 371 (c)(1),
(2), (4) Date: Apr. 11, 2003

(87) PCT Pub. No.: WO02/30872

PCT Pub. Date: Apr. 18, 2002

(65) Prior Publication Data

US 2004/0014816 A1 Jan. 22, 2004

(30) Foreign Application Priority Data

Oct. 12, 2000 (JP) ........................................ 2000-311485

(51) Int. Cl.[7] ............................................. C07C 231/00
(52) U.S. Cl. ..................... 554/61; 554/68; 514/613; 514/626; 514/824; 514/825; 514/866
(58) Field of Search ..................... 554/61, 68; 514/613, 514/626, 824, 825, 866

(56) References Cited

PUBLICATIONS

Mori, Kenji, et al. Liebigs Ann., No. 1, pp. 1–6, 1996.

*Primary Examiner*—Deborah D. Carr
(74) *Attorney, Agent, or Firm*—Birch, Stewart, Kolasch & Birch, LLP

(57) ABSTRACT

The present invention provides an aliphatic compound represented by the following formula (I) or pharmacologically acceptable salts thereof:

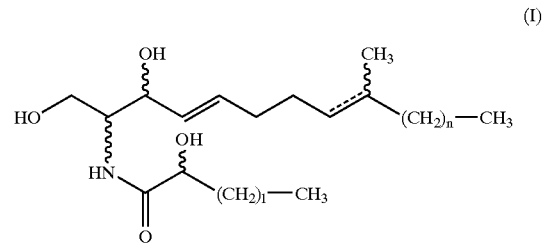

(I)

where n denotes an integer of 1 to 11, and l denotes an integer of 1 to 16, the aliphatic compound being an optical isomer of the (2R,3S,2'S) configuration when the 8-position thereof is a double bond, or an optical isomer of the (2S,3R,2'RS) configuration when the 8-position is a single bond; methods for producing the compound or pharmacologically acceptable salts thereof; and uses of the compound in the treatment of cardiovascular diseases (e.g. arteriosclerosis, cardiac diseases), cancer, rheumatism, diabetic retinopathy, and respiratory diseases.

16 Claims, 4 Drawing Sheets

ALIPHATIC COMPOUNDS, PROCESS FOR THEIR PREPARATION AND THEIR USAGE

This application is the national phase under 35 U.S.C. §371 of PCT International Application No. PCT/JP01/08992 which has an International filing date of Oct. 12, 2001, which designated the United States of America.

TECHNICAL FIELD

This invention relates to novel aliphatic compounds, methods for producing them, and pharmaceuticals comprising the aliphatic compounds as an active ingredient.

BACKGROUND ART

Alpha granules released from activated platelets during the process of hemostasis contain serotonin, ADP and the aliphatic derivative, 2-amino-3-hydroxy-4-octadecene-1-phosphate (AHOP). Serotonin shows vasoconstriction, and ADP exhibits platelet aggregation, both compounds promoting hemostasis, whereas the role of AHOP has been unknown. In recent years, endothelial differentiation gene (Edg), an orphan receptor for which AHOP is an endogenous ligand, has been discovered. The possibility is being shown that the binding of AHOP and Edg acts in directions toward promotion of arteriosclerosis, such as hemodynamic aggravation or vascular smooth muscle growth, or in directions toward the progression of respiratory diseases.

The gene of Edg was cloned as an orphan receptor in 1990 [Edg-1 (JBC, '90, 265, p. 9308)]. Then, Edg-3 (BBRC, '96, 227, p. 608) and Edg-5 (AGR16/H218) (JCB, '96, 135, p. 1071) were obtained as homologues of Edg-1, but their physiological roles remained unclear. In 1998, however, the possibility of AHOP being an endogenous ligand for Edg-1 was suggested (Science, '98, 279, p. 1552), and then Edg-3 and Edg-5 were also shown to be AHOP-specific receptors (BBRC, '99, 260, p. 263; JBC, '99, 274, 27, p. 18997).

Edg-1 on the vascular endothelial cell, when stimulated by AHOP, upregulates an adhesion protein, such as cadherin, through activation of low molecular weight GTP-binding protein Rho (Science, '98, 279, p. 1552). T lymphocyte-derived strain cells, upon stimulation by AHOP, accelerates vascular layer penetration in an in vitro pseudo-blood vessel model (EMBO J., '98, vol. 17, No. 14, p.4066). Okajima et al. conducted pseudo-blood vessel migration tests using CHO cells forced to express Edg-1 or Edg-3, and found migration to be promoted AHOP concentration-dependently in either case ('99 Congress of the Japanese Biochemical Society, A collection of the Abstracts, p. 883). On the other hand, Igarashi et al. showed that the cancer cell strain F10 underwent suppression of migration by about a maximum of 80% concentration-dependently at an AHOP concentration of $10^{-8}$ to $10^{-6}$ M in a pseudo-blood vessel model, but Edg-1 or Edg-3 was scarcely expressed, and Edg-5 was expressed, in the F10 cells ('99 Congress of the Japanese Biochemical Society). In connection with these findings, the possibility was pointed out that AHOP showed the suppression of migration because of a difference in subspecies ('99 Congress of the Japanese Biochemical Society, A collection of the Abstracts, p. 675, p. 883).

AHOP-responsive activation of MAP kinase was observed in vascular smooth muscle cells (Eur. J. Biochem., '98, 257, p. 403) or respiratory tract smooth muscle cells (Biochem. J., '99, 338, p. 643), indicating the possibility for AHOP to act in a direction toward the growth of vascular smooth muscle cells.

Sugiyama et al. administered AHOP to rats by the caudal vein route, and observed hemodynamics. They noted significant drops in two parameters, systolic blood pressure and time differential of left ventricular pressure, showing the possibility that AHOP acts in a direction toward decline of cardiac function in vivo (A collection of the Abstracts at the '00 Congress of the Japanese Pharmacological Society, p. 127).

The possibility is also pointed out that AHOP activates muscarinic receptor inward $K^+$ rectifier to cause arrhythmia ('99 Pfugers Arch-Eur J Phisiol 438, pp. 642–648). Thus, an Edg receptor antagonist can be considered to have a possibility for taking effect against arrhythmia.

The effect of AHOP on vascular endothelial cells was studied in an angiogenic animal model. This study demonstrated that angiogenesis by a growth factor, such as VEGF or FGF-2, was synergistically promoted by AHOP bound to Edg-1 or Edg-3, thus showing the possibility that Edg acts on the progression of rheumatism, solid carcinoma, or diabetic retinopathy (Cell, '99, p. 301).

The possibility has been presented that excessive inflammation or respiratory tract remodeling, caused by the binding of AHOP and Edg receptor, results in the progression of pneumonia, chronic obstructive airway disease, COPD) or respiratory hypertension (Pulmonary Pharmacology & Therapeutics, 2000, 13, p. 99).

Suramin, an agent for eradicating Protozoa Trypanosoma, is reported to show Edg-3-specific antagonism and inhibit a signal for binding of AHOP and Edg (J. B. C., '99, 274, 27, p. 18997). Suramin is shown to be therapeutically effective in arteriosclerosis pathogenesis models (Circulation, '99, Cardiovascular Res., '94, 28, p. 1166), and Edg antagonism may be involved in the mechanism of this therapeutic effect.

Considered overall, these findings show the possibilities that AHOP bound to Edg acts in promoting arteriosclerosis, as evidenced by inflammatory cell activation, vascular smooth muscle cell growth or hemodynamic aggravation, and in promoting angiogenesis in favor of progression of rheumatism, solid carcinoma, or diabetic retinopathy. That is, substances antagonizing Edg are likely to show the properties of anti-cardiovascular diseases (for example, anti-arteriosclerosis, anti-cardiac diseases (e.g. anti-arrhythmia, anti-myocardial infarction)), anti-rheumatism, anti-cancer, anti-diabetic retinopathy, and anti-respiratory diseases.

The inventors of this invention performed in-depth studies in the light of the above circumstances, and newly discovered compounds represented by formulas (I) to (V) shown below. They found that these compounds (hereinafter referred to as "compounds of the present invention") are antagonistic to Edg receptor. The present invention is based on this finding, and its object is to provide novel aliphatic compounds, methods for producing them, and pharmaceuticals comprising these compounds.

DISCLOSURE OF THE INVENTION

The present invention relates to an aliphatic compound represented by the following formula (I)

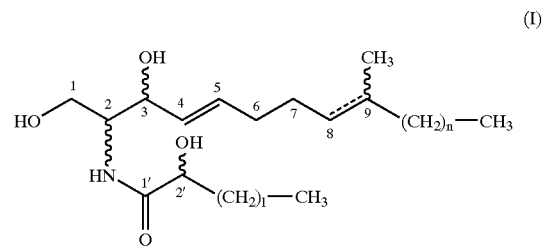

(I)

where n denotes an integer of 1 to 11, and 1 denotes an integer of 1 to 16, which is an optical isomer of the (2R,3S,2'S) configuration when the 8-position is a double bond, or an optical isomer of the (2S,3R,2'RS) configuration when the 8-position is a single bond.

In the above formula, the wavy line refers to the inclusion of any of the optical isomerisms (R), (S) and racemic modification. Herein, the upper chain is called the first chain, and the lower chain is called the second chain.

Figure 1:
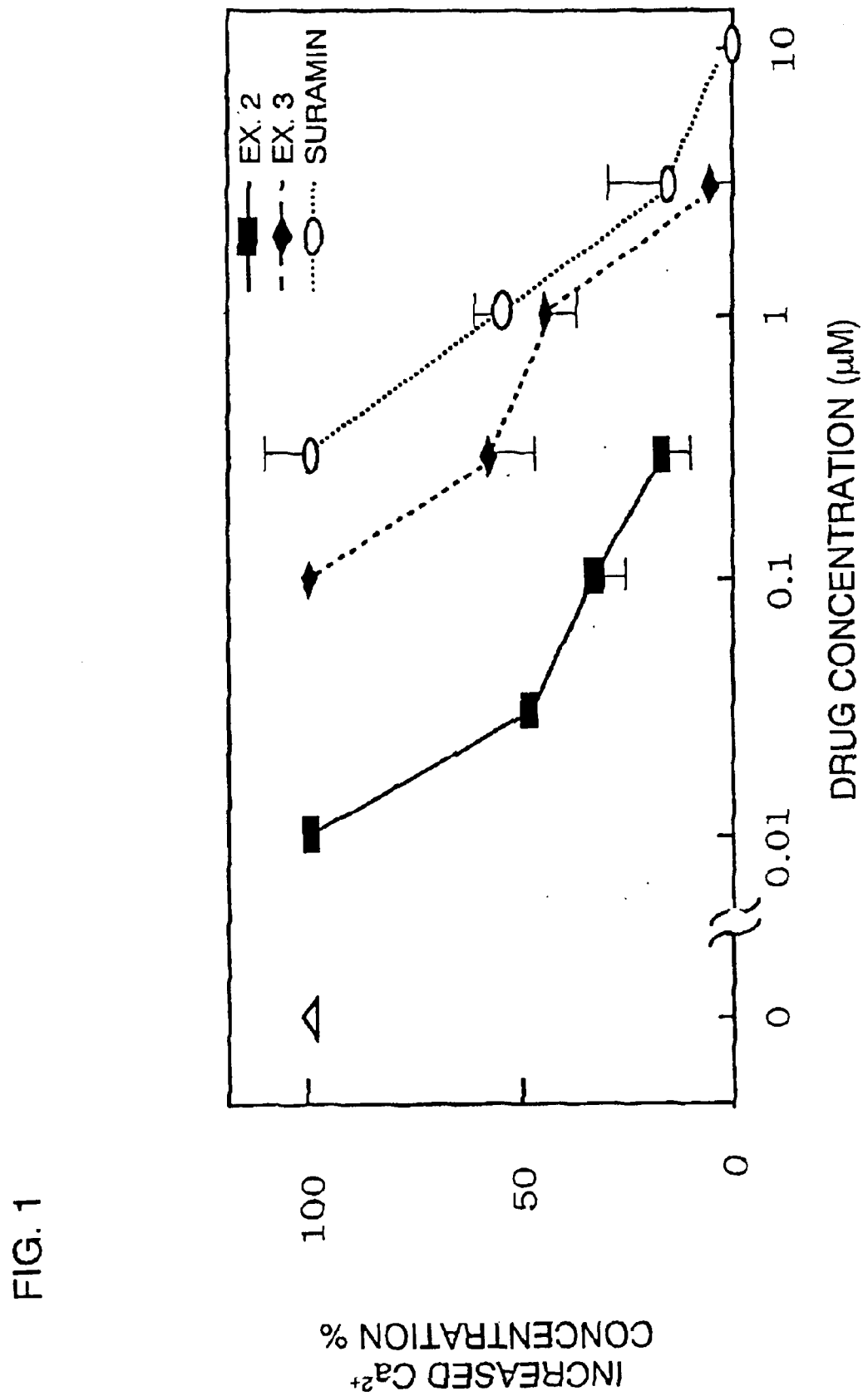
FIG. 1 is a graph showing that the compounds of the present invention are Edg-antagonistic dose-dependently (suramin: control).

In the drawing, an unfilled triangle signifies data obtained when no test substance is incorporated.

Figure 2:
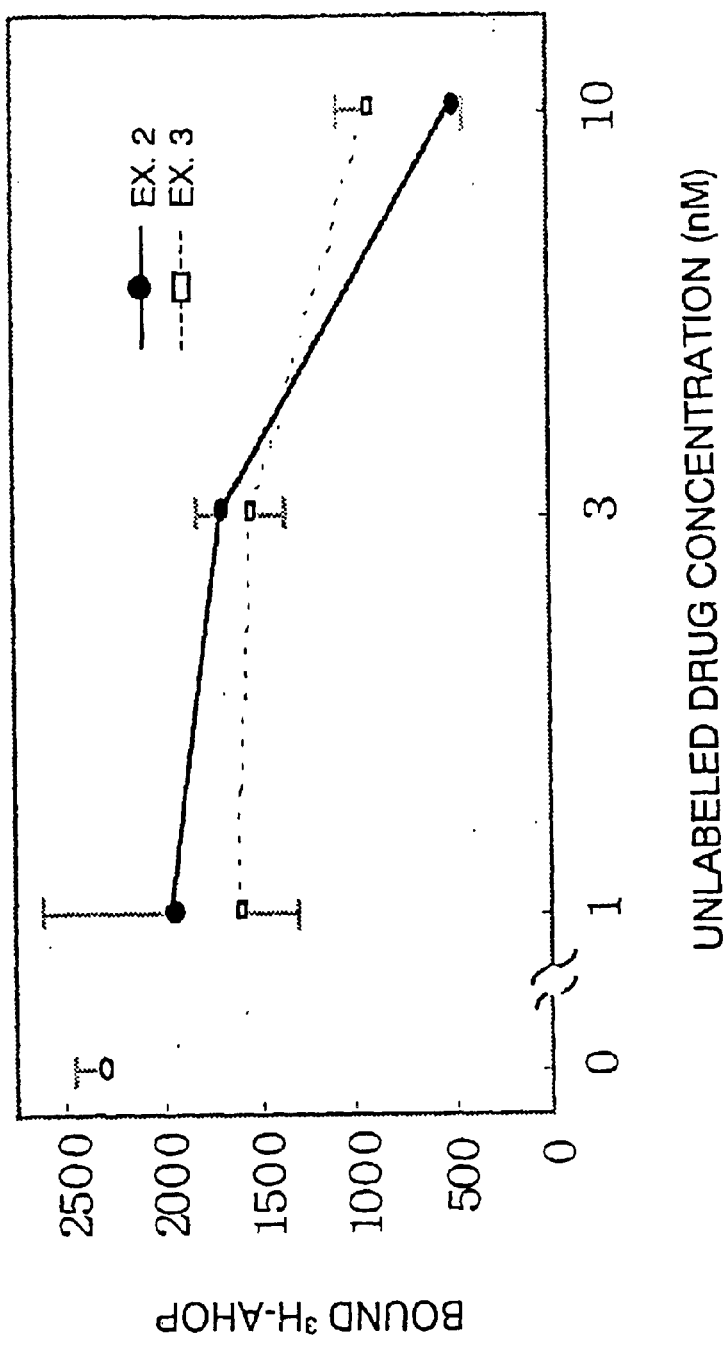

FIG. 2 is a graph in which the compounds of the present invention show an AHOP-competitive action dose-dependently.

In the drawing, an unfilled circle signifies data obtained when no test substance is incorporated.

Figure 3:
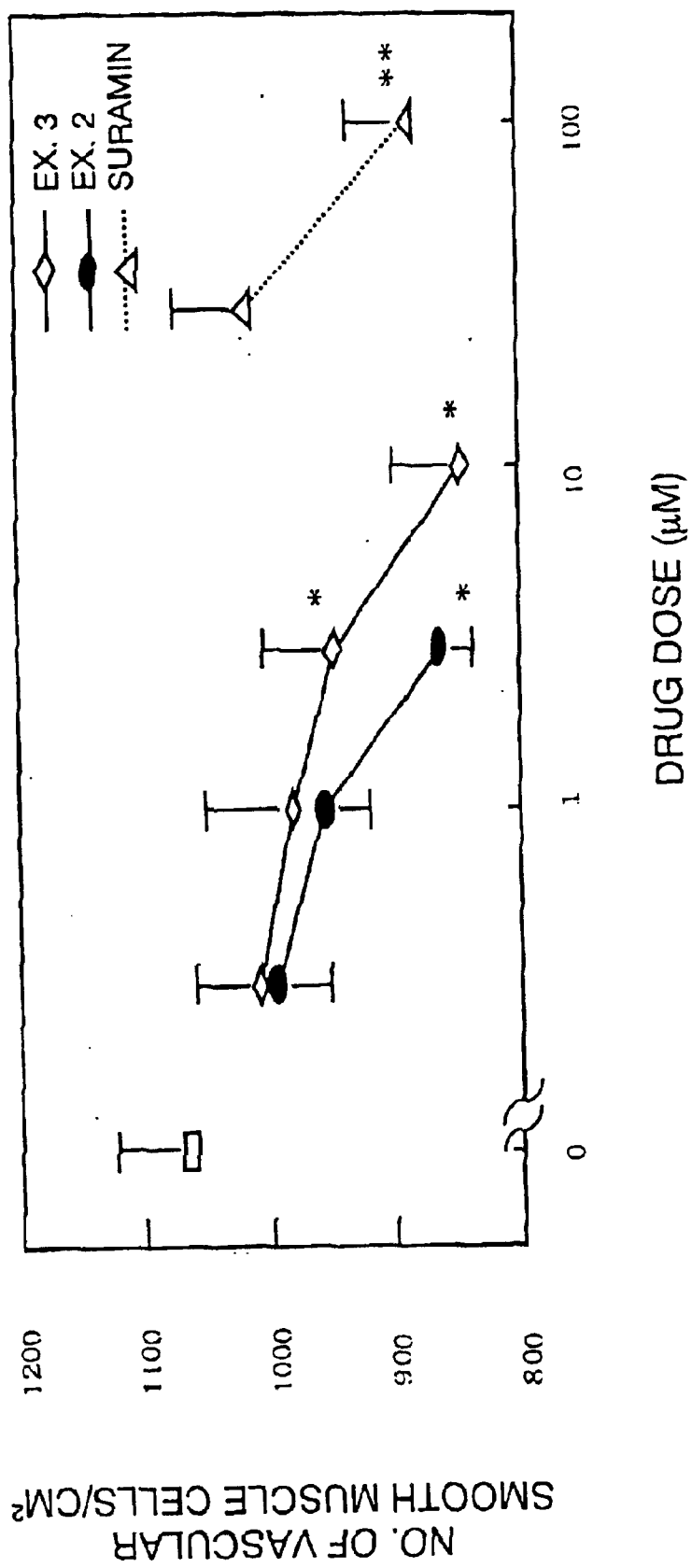

FIG. 3 is a graph in which the compounds of the present invention show the action of suppressing vascular smooth muscle cell growth dose-dependently (suramin: control).

In the drawing, an unfilled rectangle signifies data obtained when no test substance is incorporated. *: Shows significant suppression at significance level $p \leq 0.05$ against the negative control. **: Shows significant suppression at significance level $p \leq 0.01$ against the negative control.

Figure 4:
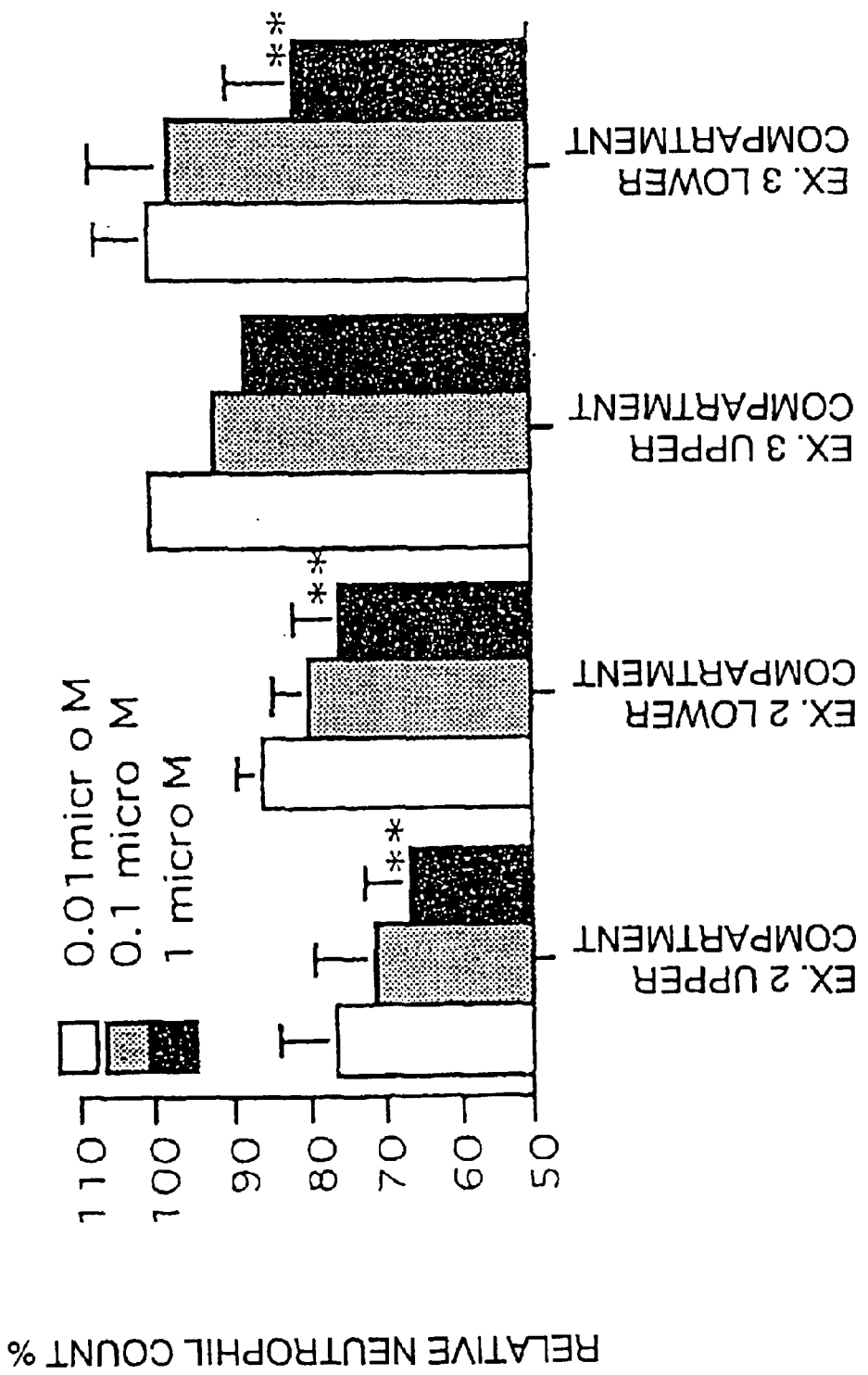

FIG. 4 shows the action of the compounds of the present invention on endothelial cell-neutrophil interaction. **: Shows significant suppression at significance level $p \leq 0.01$ against the control.

BEST MODE FOR CARRYING OUT THE INVENTION

Preferred embodiments are cited below.

The present invention provides the compound of the aforementioned formula (I) which is a compound of the following formula (II):

Formula (II)

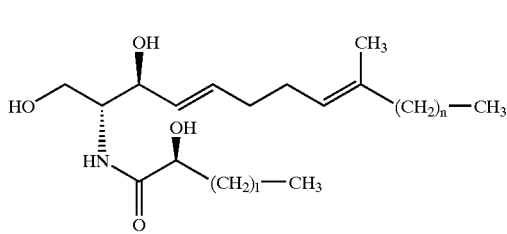

(II)

where n and l have the same meanings as those of the symbols in the compound of the formula (I).

The present invention also provides the compound of the aforementioned formula (I) which is a compound of the following formula (III):

Formula (III)

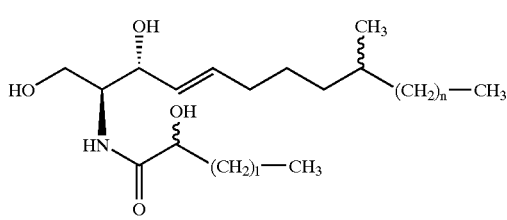

(III)

where n and l have the same meanings as those of the symbols in the compound of the formula (I).

In the compounds of the formulas (I), (II) and (III) of the present invention, preferably n is 1 to 10 and l is 1 to 15, and more preferably n is 1 to 8 and l is 1 to 13.

The present invention also provides the compound of the aforementioned formula (I) which is a compound of the following formula (IV): (4E,8E,2R,3S,2'S)-N-2'-hydroxyhexadecanoyl-9-methyl-4,8-octadecadiene-1,3-diol Formula (IV)

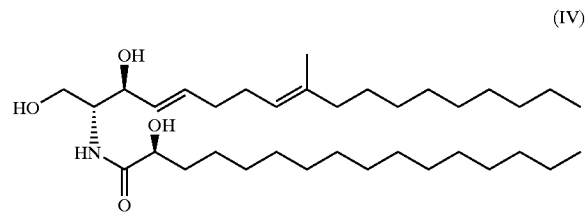

(IV)

The present invention also provides the compound of the aforementioned formula (I) which is a compound of the following formula (V): (4E,2S,3R,2'RS)-N-2'-hydroxyhexadecanoyl-9-methyl-4-octadecene-1,3-diol Formula (V)

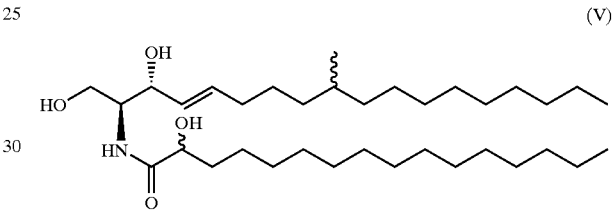

(V)

The compounds of the present invention can form pharmacologically acceptable salts thereof. The salts are not limited, and include, for example, hydrohalogenic acid salts, such as hydrofluorides, hydrochlorides, hydrobromides and hydroiodides, inorganic acid salts, such as nitrates, perchlorates, sulfates, phosphates, and carbonates, lower alkylsulfonic acid salts, such as methanesulfonates, trifluoromethanesulfonates and ethanesulfonates, arylsulfonic acid salts, such as benzenesulfonates and p-toluenesulfonates, carboxylic acid salts, such as acetates, fumarates, succinates, citrates, tartrates, oxalates and maleates, amino acid salts, such as glycine salts, alanine salts, glutamates and aspartates, and alkali metal salts, such as sodium salts and potassium salts.

The compounds of the present invention all show endothelial differentiation gene (Edg) receptor antagonism, antagonize the binding of Edg receptor agonizing substances, such as AHOP and sphingosylphosphorylcholine, to Edg receptors, and can inhibit the intracellular signal transduction system relying on these substances.

Hence, the present invention provides pharmaceuticals antagonizing endothelial differentiation gene (Edg) receptor, the pharmaceuticals comprising the compounds of the formulas (I) to (V) as an active ingredient.

Moreover, the present invention provides the pharmaceuticals for treating diseases resulting from the activation of inflammatory cells, the growth of vascular smooth muscle cells, the aggravation of hemodynamics, and angiogenesis, for example, cardiovascular diseases (e.g. arteriosclerosis, cardiac diseases (e.g. myocardial infarction, arrhythmia)), rheumatism (e.g. rheumatoid arthritis), cancer, diabetic retinopathy, and respiratory diseases (e.g. pneumonia, chronic obstructive airway disease, respiratory system hypertension).

The "treatment" includes prevention as well.

The "cardiovascular diseases" refer to diseases in which the circulatory state of blood or lymph is disturbed, resulting in disorder of a tissue or cells. Their examples are arteriosclerotic diseases (e.g. atherosclerosis), and cardiac diseases (e.g. myocardial infarction, arrhythmia).

The "respiratory diseases" refer to diseases, in which the respiratory organ, such as trachea, bronchus or lung, is disordered, and symptoms related to them. Their examples are asthma (immediate, delayed or allergic asthma), bronchial asthma, allergic rhinitis, eosinophilic infiltration, bronchitis (chronic bronchitis), respiratory tract inflammation, pulmonary emphysema, pneumonia, chronic obstructive pulmonary disease (COPD), acute respiratory distress syndrome, respiratory hypertension, dyspnea, pain, coughing, sputum, vomiting, and shortness of breath.

For use as pharmaceuticals, the compounds of the present invention may be in any forms, such as solid compositions, liquid compositions and other compositions, and optimal forms are selected according to needs. Pharmaceutical compositions can be prepared in dosage forms, such as tablets, pills, capsules, granules, powders, liquids and solutions, emulsions, suspensions, and injections, by adding excipients, bulking agents, binders, disintegrants, pH adjustors and solubilizers, which are in customary use, to the compounds of the present invention, and treating the mixtures by customary pharmaceutical manufacturing techniques. Examples of the excipients and the bulking agents are lactose, magnesium stearate, starch, talc, gelatin, agar, pectin, acacia, olive oil, sesame oil, cacao butter, ethylene glycol, and other materials which are commonly used.

To prevent the oxidation of the resulting preparations, antioxidants (e.g. tocopherol) may be added, the preparations may be included with inclusion agents, such as cyclodextrin, or the preparations may be encapsulated with a film of gelatin or the like.

Furthermore, the aforementioned compounds can be produced as O/W preparations, as described in Japanese Unexamined Patent Publication No. 6-298642, with the use of phospholipids or nonionic surfactants as emulsifying agents. The emulsifying agents can be used alone or in combination of two or more, and the amount of the emulsifying agent may be 0.001 to 10% (W/V), as desired, or preferably 0.01 to 5% (W/V).

Examples of the phospholipids are soybean-derived phospholipid, egg yolk-derived phospholipid, lysolecithin, phosphatidylcholine (lecithin), and phosphatidylserine, which can be used alone or in combination. Examples of the nonionic surfactants are, but not limited to, polyoxyethylene-polyoxypropylene block copolymer with a molecular weight of 500 to 15,000 (e.g. Pluronic F-68), polyalkylene glycol with a molecular weight of 1,000 to 10,000, polyoxyalkylene copolymer with a molecular weight of 1,000 to 20,000, hydrogenated castor oil polyoxyalkylene derivatives, castor oil polyoxyalkylene derivatives, glycerin fatty acid esters, polyglycerin fatty acid esters, sorbitan fatty acid esters, polyoxyethylene castor oil, hydrogenated castor oil, polyoxyethylene alkyl ethers, and sucrose fatty acid esters, which are preferably used alone or in combination.

The compounds of the present invention can be administered orally or parenterally in a dose of about 0.0001 to about 100 mg/kg body weight/day, which was given once daily or in several divided doses per day. This dosage can be increased or decreased appropriately depending on the type of the disease, or the age, body weight or symptoms of the patient.

The compounds of the present invention can be produced by the following methods of production:

SYNTHETIC EXAMPLE 1

The method of producing the compound of the formula (I) will be described, including a Preparation Example for starting materials for reactions.
(1) Preparation Example for Reaction Materials
(A) Synthesis of Oxazoline Aldehyde Derivative An oxazoline aldehyde derivative of the following formula can be synthesized by a conventional method:

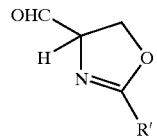

where R' represents an alkyl group or an aryl group, and R' is preferably an aryl group (for example, a phenyl group).

For example, when (L)-serine is used as a starting material, the compound can be produced in the following manner:

(L)-serine is converted to its ester (e.g. Me ester) (Ber. Dtsch. Chem. Ges. 39, 2949(1906)). The serine used here is R-serine if the optical isomerism of the first chain of the desired compound corresponds to 2R-isomer, or S-serine if the optical isomerism of the first chain of the desired compound corresponds to 2S-isomer.

Then, the resulting serine ester is reacted using an imino ether (e.g. benzimino ethyl ether) under Elliott's conditions (J. Chem. Soc. 589 (1949)) to obtain an oxazoline ester derivative. Since the oxazoline ester formed here retains the same optical isomerism as the starting serine and shows no racemization, it is advantageous in obtaining the desired optical isomer.

Then, an oxazoline aldehyde derivative is obtained from the resulting oxazoline ester derivative.

This reduction reaction is performed in an inert solvent (e.g. hexane) in the copresence of a metal hydride (e.g. DIBAL-H (diisobutylaluminum hydride)). After the reaction is terminated, the reaction mixture is extracted with a solvent (e.g. an aqueous solution of sodium potassium tartrate, and EtOAc), whereby the desired oxazoline aldehyde derivative can be obtained.

Since the resulting oxazoline aldehyde derivative is unstable, it is preferably subjected immediately to a reaction at a subsequent stage.
(B) Synthesis of (E)-Form Alkenylalane An alkenylalane of the following formula can be synthesized in the conventional manner:

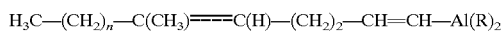

where n is as defined for the compound of the formula (I), and R represents an alkyl group, preferably i-Bu.

For example, the desired alkenylalane in which R is i-Bu can be obtained by the addition reaction of DIBAL-H with alkyne (J. Am. Chem. Soc. 95, 4098 (1973)).

This reaction can be performed in an inert solvent (e.g. hexane) at a temperature of 20 to 50° C.

Since the alkenylalane is unstable, it is preferably used, in the form of the resulting product, for a subsequent step. The alkenylalane can be easily confirmed by the substances used in the formation step and the product of the subsequent step.

The alkyne, the starting material for synthesis of the alkenylalane, can be synthesized by various methods, which include, for example, the following method:

An alcohol compound is converted into a bromide compound by an ordinary method via a tosylate. The bromide compound is converted into a nitrile compound, and further reduced in the copresence of a metal hydride (e.g. DIBAL-H) to obtain an aldehyde compound. Then, the aldehyde is converted into a dibromoalkene by the method of Corey et al. (Tetrahedron Lett. 3769 (1972)) using $Ph_3P$ and $CBr_4$, whereafter an alkyne is synthesized in the presence of a strong base (e.g. n-BuLi).

(2) Synthesis of the Compound of the Formula (I)

A synthesis scheme for the compound of the formula (I) is indicated below.

aldehyde derivative and the alkenylalane is in the R- and S-configurations. Thus, it is preferred to separate the diastereomer corresponding to the desired compound (if the optical isomerism at the 3-position of the first chain of the desired compound corresponds to 3R-isomer, the R-compound is separated, and if the desired compound is 3S-isomer, the S-compound is separated).

Separation of the diastereomer can be carried out using ordinary chromatography.

Second step: The above product is ring-opened at its oxazoline ring to obtain a compound having an $NH_2$ group and an

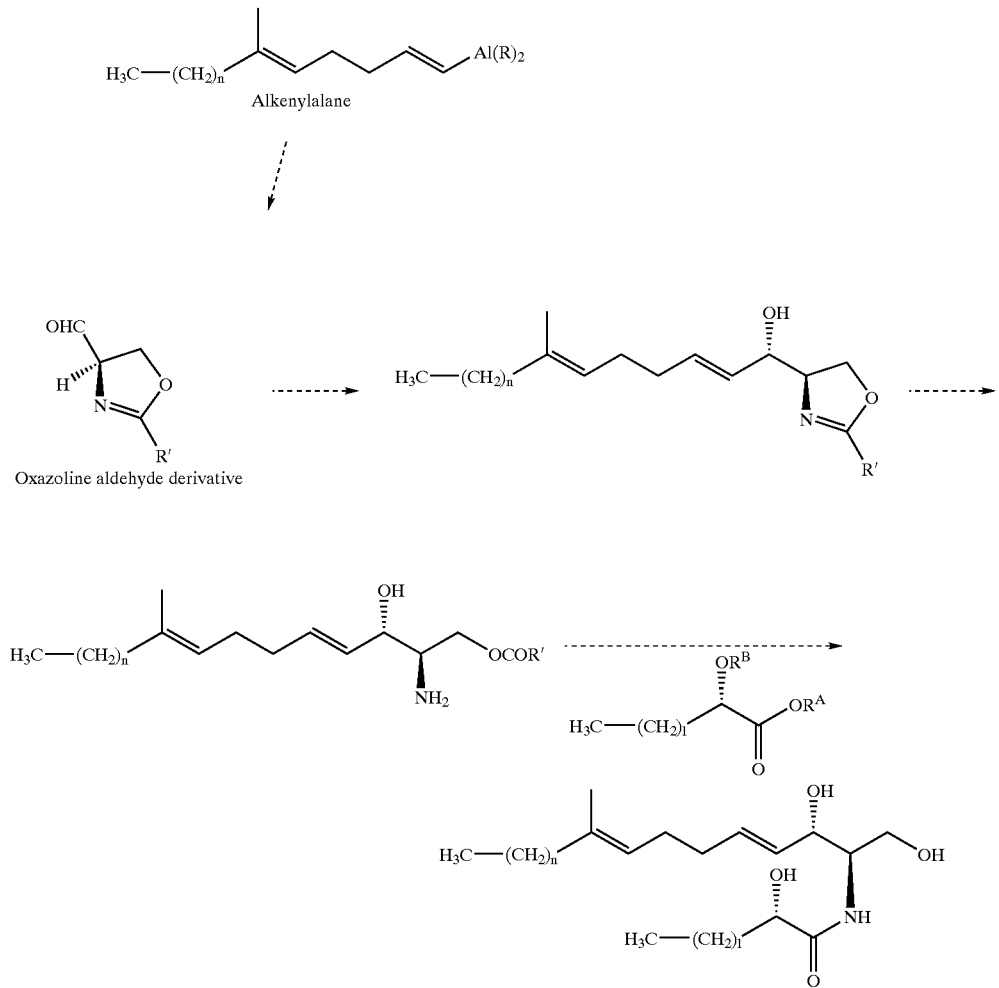

Synthetic Example 1
((2R,3S,2'S) optical isomerism with double bond at 8-position))

First step: The oxazoline aldehyde derivative obtained in (1)(A) is alkenylated with the alkenylalane obtained in (1)(B) to obtain a diastereomer mixture. The oxazoline aldehyde derivative used here is one having the same optical isomerism as that at the 2-position of the first chain of the desired compound (if the desired compound is 2R-isomer, an R-compound is used, and if the desired compound is 2S-isomer, an S-compound is used).

This reaction can be performed in an inert solvent (e.g. ether) at a temperature of −5 to 10° C.

The diastereomer mixture formed by this reaction contains two compounds in which the optical isomerism of the OH group formed by the reaction between the oxazoline —OC(=O)R' group. Ring opening can be performed in the presence of an acid (e.g. diluted HCl).

Third step: After ring opening, the product is selectively N-acylated with an acylating agent having the same optical isomerism as that at the 2'-position of the second chain of the desired compound. Then, a —C(=O)R' group is eliminated, whereby the compound of the formula (I) can be synthesized.

As the acylating agent, there can be used an ester (e.g. p-nitrophenyl ester) of $H_3C$—$(CH_2)_l$—CH(OH)C(=O)—OH (where l is as defined for the compound of the formula (I)). The hydroxyl group of the acylating agent is preferably protected (e.g., with acetyl (Ac)).

The selective N-acylation can be performed in a basic solvent (e.g. pyridine) at a temperature of 30 to 45° C.

The elimination of the —C(=O)R' group can be performed using a base (e.g. NaOH), and if the hydroxyl group is protected with Ac as mentioned above, the Ac group can also be eliminated simultaneously with this elimination.

SYNTHETIC EXAMPLE 2

The method of producing the compound of the formula (II) will be described, including a Preparation Example for reaction materials.

(1) Preparation Example for Reaction Materials (A) Synthesis of HC≡C—(CH$_2$)$_2$—CH=C(CH$_3$)—(CH$_2$)$_n$CH$_3$ in (E)-Form (E)-6-methyl-5-pentadecen-1-yne with n=8 will be taken as an example for the purpose of explanation. The captioned compound having other definition for n (n is as defined for the compound of the formula (II)) can be synthesized in the same manner as in reactions (to be described below) by using H$_3$CC(=O)(CH$_2$)$_n$CH$_3$ instead of 2-undecanone.

The method mentioned in Synthetic Example 1 can be used, but here the following method is used:

By subjecting 2-undecanone to Horner-Wittig reaction, a geometric isomer of methyl 3-methyl-2-dodecenoate is obtained.

This ester is alcoholized in the presence of a metal hydride (e.g. LiAlH$_4$), and thereby obtained as an E/Z mixture containing an alcohol, i.e. (E)-3-methyl-2-dodecen-1-ol. This mixture is subjected to silica gel column chromatography to separate the (E)-isomer.

Then, the hydroxyl group of the (E)-isomer is substituted by bromine to obtain (E)-1-bromo-3-methyl-2-dodecene. This reaction can be performed under reaction conditions for substituting a hydroxyl group by bromine. For example, the reaction can be performed by causing bromine to act on the (E)-isomer in an inert solvent (e.g. acetonitrile) in the presence of phosphine (e.g. triphenylphosphine).

Then, (E)-1-bromo-3-methyl-2-dodecene is reacted with a Grignard reagent prepared from a propargyl halide (e.g. propargyl bromide) to obtain (E)-6-methyl-5-pentadecen-1-yne. This reaction can be performed in an inert solvent (e.g. diethyl ether) at a temperature of 0 to 5° C. in the presence of a catalyst (e.g. CuCl).

(B) Synthesis of N-Protected (R)-Formyloxazolidine Derivative

An N-protected (R)-formyloxazolidine derivative of the following formula can be synthesized by the conventional method. For example, it can be synthesized from (R)-serine by the method of Mori et al. (Tetrahedron 1985, 41, 2379–2386).

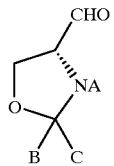

where A represents a protective group for N, and B and C each represent an alkyl group (e.g. a methyl group).

Examples of the protective group A for N are groups, such as benzyloxycarbonyl (Z), t-butoxycarbonyl (Boc), t-aminooxycarbonyl (Aoc), isobornyloxycarbonyl, p-methoxybenzyloxycarbonyl, 2-chlorobenzyloxycarbonyl, adamantyloxycarbonyl, trifluoroacetyl, phthaloyl, formyl, o-nitrophenylsulfenyl, and diphenylphosphinothioyl.

Preferably, Boc is used.

(2) Synthesis of the Compound of the Formula (II)

A synthesis scheme for the compound of the formula (II) is indicated below.

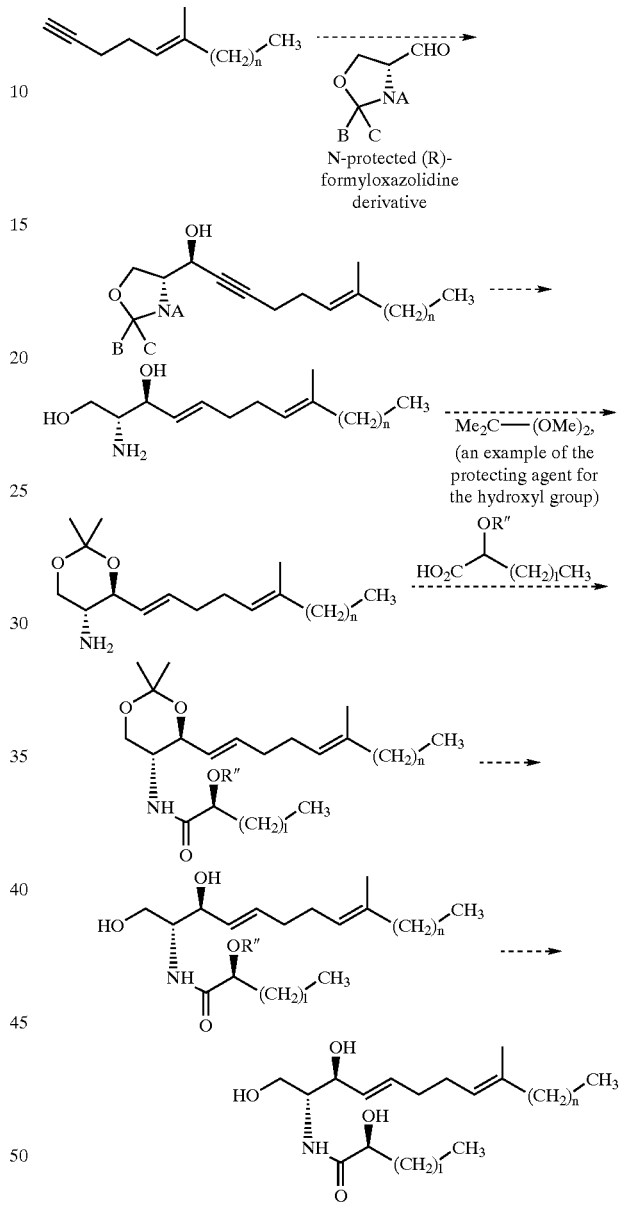

First step: The HC≡C—(CH$_2$)$_2$—CH=C(CH$_3$)—(CH$_2$)$_n$CH$_3$ in (E)-form obtained in (1)(A) is reacted with the N-protected (R)-formyloxazolidine derivative obtained in (1)(B).

The reaction in the first step can be performed in an inert solvent (for example, THF) at a temperature of −10 to −30° C. in the presence of a base (e.g. n-butyl lithium).

Second step: The triple bond of the product in the first step is reduced to an (E)-type double bond. Simultaneously, the oxazolidine is deprotected while it is ring-opened, to obtain a compound having an NH$_2$ group and an OH group.

The reaction in the second step can be performed in an inert solvent (for example, THF) at a temperature of −70 to −78° C. using an alkali metal and an amine (e.g. lithium in the presence of ethylamine).

Third Step:
(1) The product in the second step is treated with a protecting agent for a hydroxyl group.

For example, 2,2-dimethoxypropane can be used as the protecting agent for a hydroxy group. This reaction can be performed in an inert solvent (e.g. trichloromethane) in the presence of an acid catalyst (e.g. pyridinium p-toluenesulfonate).
(2) Then, the protected compound is reacted with a carboxylic acid compound of the following formula:

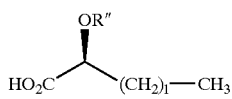

where R" represents a protective group for OH, and l has the same meaning as in the compound of the formula (II).

This reaction can be performed in an inert solvent (e.g. dry dichloromethane) in the presence of a dehydration condensation agent (e.g. dicyclohexylcarbodiimide and 1-hydroxybenzotriazole).

The carboxylic acid compound used here can be synthesized by the method of Mori et al. (Liebigs Ann. Chem. 1994, 41–48), and an OH-protecting group, e.g., tert-butyldiphenylsilyl (TBDPS), can be named as R".

Fourth step: The protective group for the hydroxyl group is subjected to deprotection, and the R" group is eliminated.

Deprotection of the protective group for the hydroxyl group can be performed in an inert solvent (e.g. $CH_2Cl_2$ and MeOH) in the presence of an acid catalyst (e.g. pyridinium p-toluenesulfonate). Elimination of the TBDPS can be performed in an inert solvent (e.g. THF) using a fluorine anion (e.g. tetra-n-butylammonium fluoride).

SYNTHETIC EXAMPLE 3

The method of producing the compound of the formula (III) will be described, including a Preparation Example for reaction materials.
(1) Preparation Example for Reaction Materials
(A) Synthesis of $HO-CH_2-CH=C(CH_3)-(CH_2)_nCH_3$ This compound can be obtained from $H_3CC(=O)(CH_2)_nCH_3$ (where n has the same meaning as in the compound of the formula (III)) in the same manner as in Synthetic Example 2.
(B) Synthesis of N-Protected (S)-Formyloxazolidine Derivative An N-protected (S)-formyloxazolidine derivative of the following formula can be synthesized by the conventional method. For example, it can be synthesized from (S)-serine in the same manner as mentioned in Synthetic Example 2.

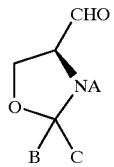

where A represents a protective group for N, and B and C each represent an alkyl group (e.g. a methyl group).

Examples of the protective group A for N are groups, such as benzyloxycarbonyl (Z), t-butoxycarbonyl (Boc), t-aminooxycarbonyl (Aoc), isobornyloxycarbonyl, p-methoxybenzyloxycarbonyl, 2-chlorobenzyloxycarbonyl, adamantyloxycarbonyl, trifluoroacetyl, phthaloyl, formyl, o-nitrophenylsulfenyl, and diphenylphosphinothioyl.

Preferably, Boc is used.
(2) Synthesis of the Compound of the Formula (III)

A synthesis scheme for the compound of the formula (III) is indicated below.

Synthetic Example 3

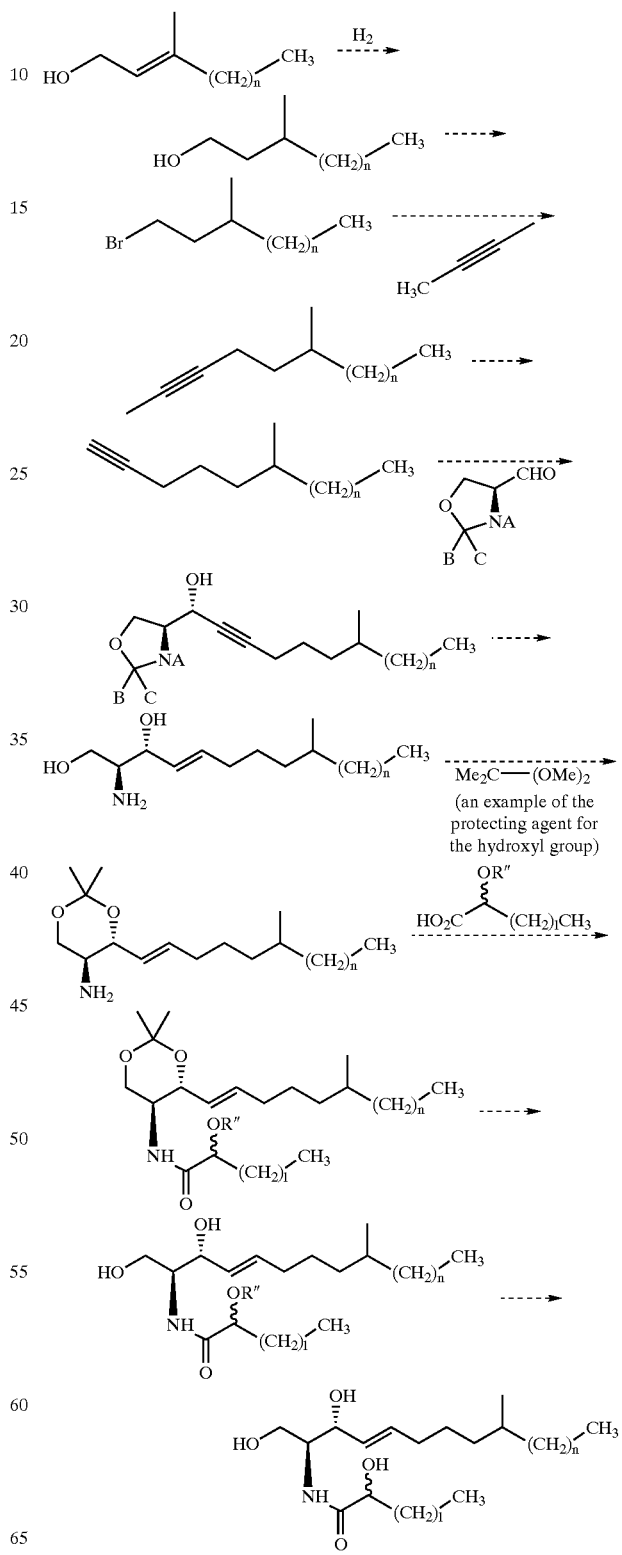

First step: The unsaturated moiety of the HO—CH$_2$—CH═C(CH$_3$)—(CH$_2$)$_n$CH$_3$ obtained in (1)(A) is saturated by catalytic reduction.

This reaction can be performed using various catalysts commonly used in catalytic reduction. For example, a palladium catalyst (e.g. palladium-carbon, Pd—C) can be used.

Second step: The hydroxyl group of the product in the first step is substituted by bromine.

Bromination can be performed by a method capable of brominating an alcohol. For example, bromination can be performed by converting the product into a tosylate, and then brominating it.

In this case, the product can be reacted with p-toluenesulfonyl chloride in an inert solvent (e.g. pyridine) to obtain a tosylate, and then the tosylate can be reacted in the presence of a bromide (e.g. sodium bromide) in an inert solvent (e.g. a dimethylformamide (DMF) solution).

Third step: The bromine of the product in the second step is substituted by CH$_3$—C≡C—.

A reaction material for use in the substitution by CH$_3$—C≡C— may, for example, be CH$_3$—C≡C—Li. In the case of CH$_3$—C≡C—Li, the reaction in the third step can be performed, for example, in the following manner:

To a solution of propyne in an inert solvent (e.g. THF solution), a ligand (e.g. tetramethylethylenediamine (TMEDA)) is added (preferably under Ar). To the mixture, an alkyl lithium (e.g. n-BuLi) is added to obtain CH$_3$—C≡C—Li. The reaction temperature is preferably –78 to 0° C.

Then, a solution (e.g. a mixture of hexamethylphosphoramide (HMPA) and THF) of the product in the second step is added to the above reaction mixture, whereby the substitution can be performed. On this occasion, the reaction temperature is preferably –78 to 20° C.

Fourth step: The location of the triple bond of the product in the third step is shifted to the terminal to obtain a compound terminated with the triple bond.

The reaction in the fourth step can be performed, for example, in the following manner:

An alkali metal (e.g. lithium) is added to an amine base (e.g. 1,3-diaminopropane) (preferably under Ar). This reaction is preferably performed at –78 to –70° C.

Then, a strongly basic alcoholate (e.g. potassium t-butoxide) is added, and the product in the third step is added, whereby the reaction is performed. This reaction is preferably carried out at 15 to 25° C.

Fifth step: The N-protected (S)-formyloxazolidine derivative obtained in (1)(B) is reacted with the product in the fourth step.

The reaction in the fifth step can be performed in an inert solvent (e.g. THF) at a temperature of –15 to –28° C. in the presence of a base (e.g. n-butyl lithium).

A sixth step and subsequent steps can be performed in the same manner as in the second and subsequent steps of Synthetic Example 2.

Sixth step: The triple bond of the product in the fourth step is reduced to an (E)-type double bond. Simultaneously, the oxazolidine is deprotected while it is ring-opened, to obtain a compound having an NH$_2$ group and an OH group.

Seventh step: This compound having the (E)-type double bond is treated with a protecting agent for a hydroxyl group, and the protected compound is reacted with a carboxylic acid compound of the following formula:

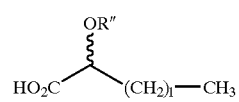

where R″ represents a protective group for OH, and l has the same meaning as in the compound of the formula (III).

The carboxylic acid compound used here can be synthesized in the same manner as in Synthetic Example 2.

Eighth step: The protective group for the hydroxyl group is subjected to deprotection, and the R″ group is eliminated.

EXAMPLES

The present invention will be described in further detail by working examples, which in no way limit the technical scope of the invention.

Example 1

Synthesis of (4E,8E,2R,3S,2′S)-N-2′-hydroxyhexadecanoyl-9-methyl-4,8-octadecadiene-1,3-diol A reaction scheme of Example 1 is shown below.

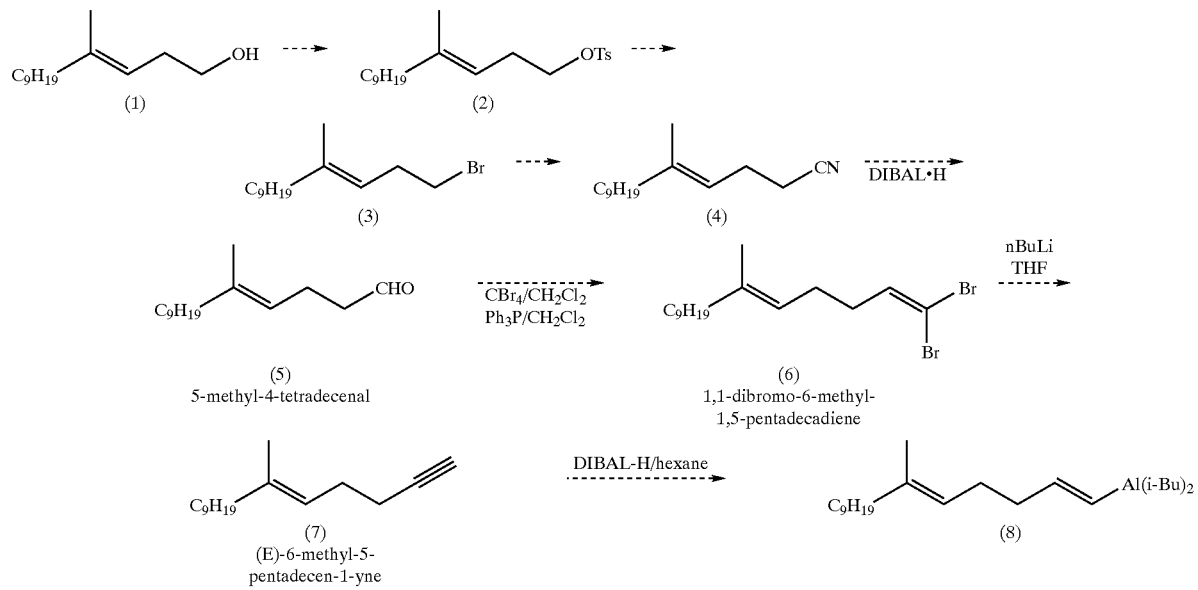

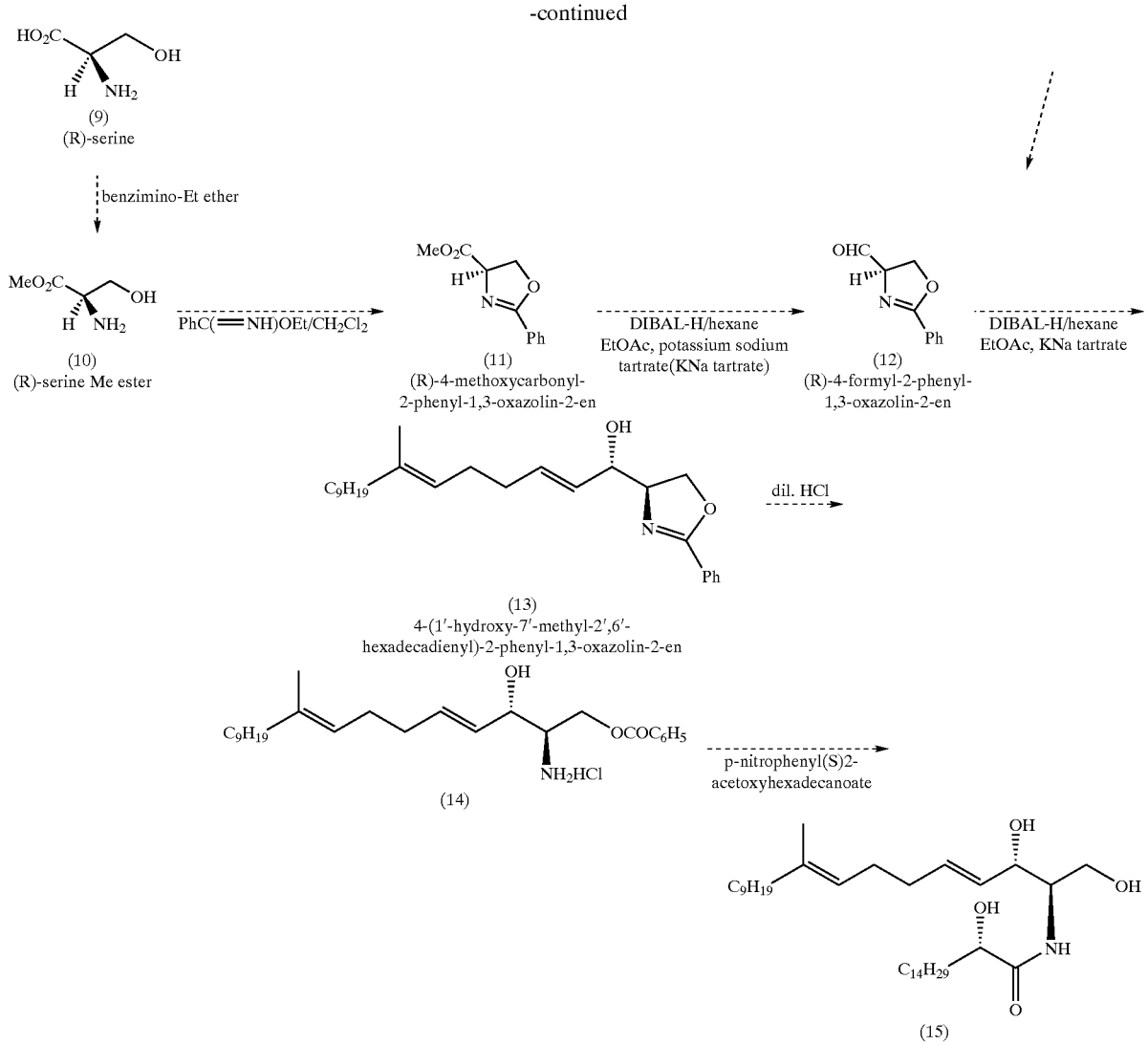

(1) Preparation of Reaction Materials
(A) Synthesis of Alkenylalane (8)

p-TsCl (45 g, 236 mmols) was added to a stirred and cooled pyridine (120 ml) solution of (E)-4-methyl-3-tridecen-1-ol (1) (33 g, 155 mmols). The mixture was stirred for 8 hours. Then, the mixture was poured into ice water (500 ml), and extracted with ether (500 ml). The ether solution was washed with 2N—HCl, a saturated aqueous solution of NaHCO$_3$, and a saturated aqueous solution of sodium chloride, dried (MgSO$_4$), and concentrated in a vacuum. The residue in crude oily form, (E)-4-methyl-3-tridecene-1-tosylate (2) (58 g), was dissolved in DMF (250 ml).

To the solution, LiBr (40 g, 460 mmols) was added, and the mixture was stirred for 18 hours at room temperature. Then, the reaction mixture was poured into ice water (1 L), and extracted with ether (300 ml×3). The ether solution was washed with water, dried (MgSO$_4$), and concentrated in a vacuum. The residue was distilled to obtain 38.3 g (93.4%) of (E)-1-bromo-4-methyl-3-tridecene (3).

A mixture of the (E)-1-bromo-4-methyl-3-tridecene (3) (38.0 g, 138 mmols) and KCN (11.5 g, 176 mmols) in DMF (100 ml) and water (30 ml) was stirred for 24 hours at 70° C. Then, the mixture was poured into ice water (1 L) and extracted with ether (500 ml). The ether solution was washed with water, dried (MgSO$_4$), and concentrated in a vacuum. The residue was subjected to silica gel chromatography, and eluted with n-hexane-ether (100:1) to obtain 30.0 g (98%) of (E)-5-methyl-4-tetradecenenitrile (4) as oily matter.

To a cooled and stirred ether (700 ml) solution of the (E)-5-methyl-4-tetradecenenitrile (4) (30.0 g, 136 mmols), an n-hexane solution of DIBAL-H (1.7 M, 123 ml, 209 mmols) was added dropwise at −60° C. under an argon gas. The mixture was stirred for 1 hour at −60° C. and for 3 hours at room temperature. The excess reagent was quenched with the addition of HCO$_2$Et (5 ml). After 30 minutes of stirring, the mixture was poured into a saturated aqueous solution of NH$_4$Cl (1.5 L). The resulting mixture was stirred for 20 minutes, acidified with a 20% aqueous solution (1 L) of H$_2$SO$_4$, and extracted with ether. The ether solution was washed with water, dried (MgSO$_4$), and concentrated in a vacuum. The oily residue was subjected to chromatography on Florisil (450 g), and eluted with n-hexane-ether (50:1) to obtain 29.0 g (95.4%) of (E)-5-methyl-4-tetradecenal (5).

A dichloromethane solution (100 ml) of CBr$_4$ (85 g, 256 mmols) was added dropwise to a stirred and ice-cooled dichloromethane solution (300 ml) of Ph$_3$P (138 g, 526 mmols). To the mixture, a dichloromethane solution (100 ml) of the (E)-5-methyl-4-tetradecenal (5) (29.0 g, 129 mmols) was added while being cooled at 0° C. and stirred, followed by stirring the mixture for 15 minutes at 0° C. The reaction of this mixture was terminated by ice-cooled water (100 ml), and after 20 minutes of stirring, the organic layer was separated. The organic solution was dried (magnesium sulfate), and then concentrated in a vacuum. The residue was triturated with pentane (1 L), and insoluble $Ph_3PO$ was removed by filtration. The filtrate was concentrated in a vacuum, and then the oily residue was subjected to silica gel column chromatography, and eluted with n-hexane to obtain 38.1 g (77.6%) of oily (E)-1,1-dibromo-6-methyl-1,5-pentadecadiene (6).

To a stirred and cooled THF (400 ml) solution of the (E)-1,1-dibromo-6-methyl-1,5-pentadecadiene (6) (37.0 g, 97.6 mmols), an n-hexane solution of n-BuLi (1.5 M, 150 ml, 225 mmols) was added dropwise at −70° C. under an Ar gas. The mixture was stirred for 1 hour at −70° C. and for 1.5 hours at room temperature. Then, the reaction mixture was poured into 1.5 liters of ice water, and extracted with n-hexane. The hexane solution was washed with water, dried with sodium sulfate, and concentrated in a vacuum. The residue was subjected to silica gel column chromatography, and eluted with n-hexane to obtain 18.9 g (88.0%) of (E)-6-methyl-5-pentadecen-1-yne (7) as oily matter.

To a stirred n-hexane (5 ml) solution of the (E)-6-methyl-5-pentadecen-1-yne (7) (1.4 g, 6.4 mmols), a solution of DIBAL-H (1.7 M, 3.8 ml, 6.4 mmols) in n-hexane was added dropwise in the presence of an Ar gas. The mixture was stirred for 2 hours at 50° C., and the resulting solution of alkenylalane (8) was cooled with an ice bath.

(B) Synthesis of (R)-4-formyl-2-phenyl-1.3-oxazolin-2-en

An HCl gas was vigorously bubbled in a dry MeOH solution of (R)-serine (9) (25 g, 238 mmols) until the solution became very hot (spontaneous reflux). The solution was allowed to stand for 16 hours at room temperature, and then MeOH was removed under vacuum. The residue was triturated with ether (50 ml). The resulting (R)-serine Me ester (10) in solid form was recovered on a filter paper, washed with ether (50 ml), and dried in a vacuum. Recrystallization from MeOH-ether (1:3) gave 35.9 g (97.0%) of (R)-serine Me ester (10).

A solution of PhC(=NH)OEt (60 g, 0.4 mol) in dichloromethane (100 ml) was added to an aqueous solution (20 ml) of the (R)-serine Me ester (10) in HCl (33 g, 0.21 mol). The mixture was vigorously stirred for 24 hours at room temperature. The mixture was filtered, and the filtrate was diluted with dichloromethane (100 ml) and water (50 ml). The organic solution was separated, dried using magnesium sulfate, and concentrated in a vacuum. The residue was distilled to obtain 33.3 g of (R)-4-methoxycarbonyl-2-phenyl-1,3-oxazolin-2-en (11). b.p.: 120–123° C./0.09 mm, $[\alpha]_D^{21}$=−118.20° (c=1.13, $CHCl_3$).

To a stirred and cooled solution of the (R)-4-methylcarbonyl-2-phenyl-1,3-oxazolin-2-en (11) (1.4 g, 6.8 mmols) in toluene (30 ml) and n-hexane (5 ml), a solution of DIBAL-H (1.7 M, 6.0 ml, 10.2 mmols) in n-hexane was added dropwise at −70° C. under an Ar gas. The mixture was stirred for 2 hours at −70° C. Then, MeOH (1 ml) was added dropwise at −70° C., and the mixture was stirred for 30 minutes. Then, an EtOAc solution (10 ml) and a saturated aqueous solution (20 ml) of potassium sodium tartrate were added to terminate the reaction. By removing the cooling bath, the temperature was raised to room temperature. The mixture was partitioned between EtOAc (500 mL) and a saturated aqueous solution (1.5 L) of potassium sodium tartrate. The organic solution was dried over magnesium sulfate, and then concentrated in a vacuum to obtain 1.4 g (quantitative) of (R)-4-formyl-2-phenyl-1,3-oxazolin-2-en (12) as a crude yellow oil.

(2) Synthesis of the Compound of Example 1

Step 1: The (R)-4-formyl-2-phenyl-1,3-oxazolin-2-en (12) (1.2 g, about 5.8 mmols) obtained in (1)(B), which was dissolved in ether (5 ml), was added to a solution of the alkenylalane (8) obtained in (1)(A), and the mixture was stirred at 0 to 5° C. The temperature was returned to room temperature, and stirring was continued for 2 hours. The mixture was poured into a saturated potassium sodium tartrate solution (400 ml), and extracted with EtOAc (400 ml). The EtOAc solution was dried over magnesium sulfate, and then concentrated in a vacuum. TLC analysis (n-hexane:ether,3:7) of the residue showed it to be a mixture of two compounds, one of which had Rf of 0.56, the other having Rf of 0.39. These two compounds were subjected to silica gel column chromatography. On elution with n-hexane:ether(3:1), a nonpolar crystalline isomer, 404 mg (21.4% from the compound (7)) of (1'R)-isomer (recrystallized from n-hexane), was obtained first. Further elution with the same solvent gave a polar isomer, 294 mg (15.6% from the compound (7)) of a corresponding (1'S)-isomer, namely, (4R,1'S)-4-(1'-hydroxy-7'-methyl-2',6'-hexadecadienyl)-2-phenyl-1,3-oxazolin-2-en isomer (13). This crystalline isomer being an erythro-isomer was confirmed by converting it later into a final product in (4E,8E) form.

Step 2: 2N—HCl (1 ml) was added to a THF solution (4 ml) of the (4R,1'S)-4-(1'-hydroxy-7'-methyl-2',6'-hexadecadienyl)-2-phenyl-1,3-oxazolin-2-en (13) (160 mg, 0.4 mmol). The mixture was stirred for 20 hours at room temperature. The reaction mixture was diluted with ice water (10 ml), and extracted with $CHCl_3$-MeOH (87:13, 25 ml×3). The organic solution was dried over magnesium sulfate, and concentrated in a vacuum to obtain about 200 mg (quantitative) of a compound (14).

Step 3: The compound (14) was dissolved in pyridine (1 ml), and a pyridine solution (1 ml) of p-nitrophenyl(S)-2-acetoxyhexadecanoate (400 mg, 0.92 mmol) was added to the solution, followed by stirring the mixture for 20 hours at 45° C. The solvent was removed under vacuum, and the residue was subjected to silica gel column chromatography. Elution with n-hexane:ether(2:1) gave a yellow oil. The small amount of oil in n-hexane solution precipitated crystals of (4E,8E,2R,3S,2'S)-N-2'-acetoxyhexadecanoyl-1-O-benzoyl-9-methyl-4,8-octadecadiene-1,3-diol. Recrystallization of the crystals from n-hexane gave 184 mg of a pure product.

This product (425 mg, 0.6 mmol) was dissolved in $CHCl_3$ (30 ml), and the solution was added to an MeOH solution (0.3N, 20 ml) of NaOH, followed by stirring the mixture for 15 minutes at room temperature. The mixture was poured into ice-cooled water (100 ml) and extracted with $CHCl_3$ (300 ml×2). The $CHCl_3$ solution was washed (a saturated aqueous solution of sodium chloride), dried (magnesium sulfate), and concentrated under vacuum, whereafter the residue was subjected to silica gel column chromatography. Elution with $CHCl_3$-EtOAC (3:2) gave a solid, which was recrystallized from n-hexane to obtain 248 mg (73.4%) of (4E,8E,2R,3S,2'S)-N-2'-hydroxyhexadecanoyl-9-methyl-4,8-octadecadiene-1,3-diol (15). mp: 62.0–63.0° C., $[\alpha]_D^{23}$=−7.3 (c=0.61, $CHCl_3$)

Example 2

Synthesis of (4E,8E,2R,3S,2'S)-N-2'-hydroxyhexadecanoyl-9-methyl-4.8-octadecadiene-1,3-diol (1) Preparation of Reaction Materials (A) Synthesis of N-Boc-Protected (R)-Formyloxazolidine Derivative An N-Boc-protected (R)-2,2-dimethyl-4-formyloxazolidine was synthesized from (R)-serine in accordance with a scheme illustrated below.

(B) Synthesis of a Tert-Butyldiphenylsilyl (TBDPS) Protected Acid (2S)-2-(tert-butyldiphenylsilyloxy)hexadecanoic acid was synthesized in accordance with a scheme shown below.

Synthesis of N-Boc-protected (R)-formyloxazolidine derivative

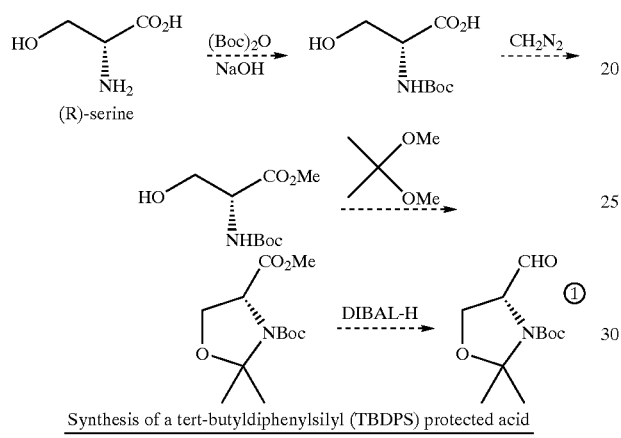

Synthesis of a tert-butyldiphenylsilyl (TBDPS) protected acid

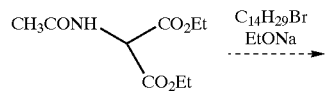

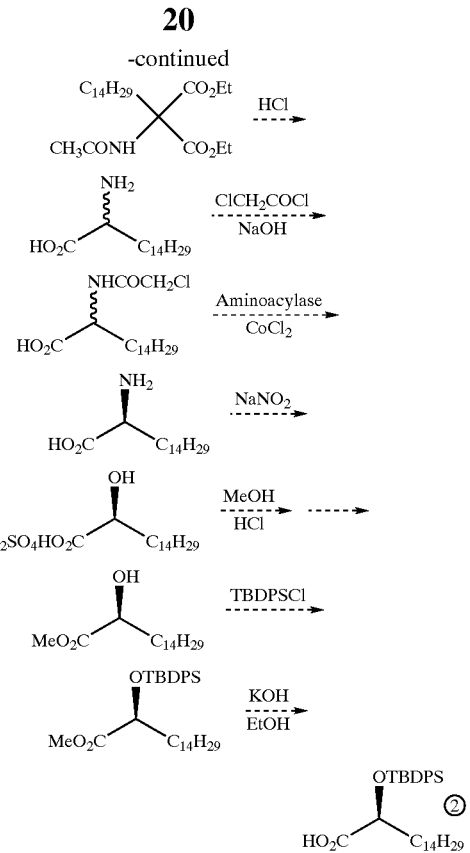

(2) Synthesis of Starting Materials and the Compound of Example 2

A synthesis scheme is shown below.

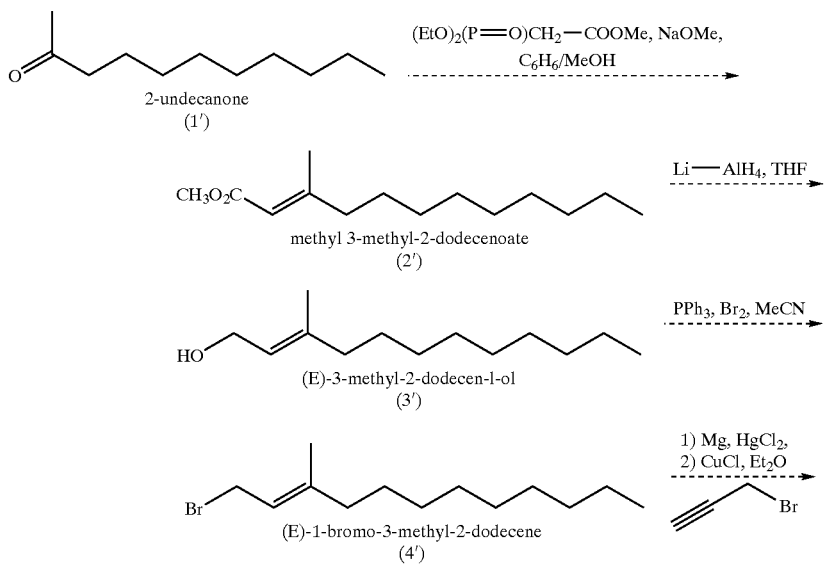

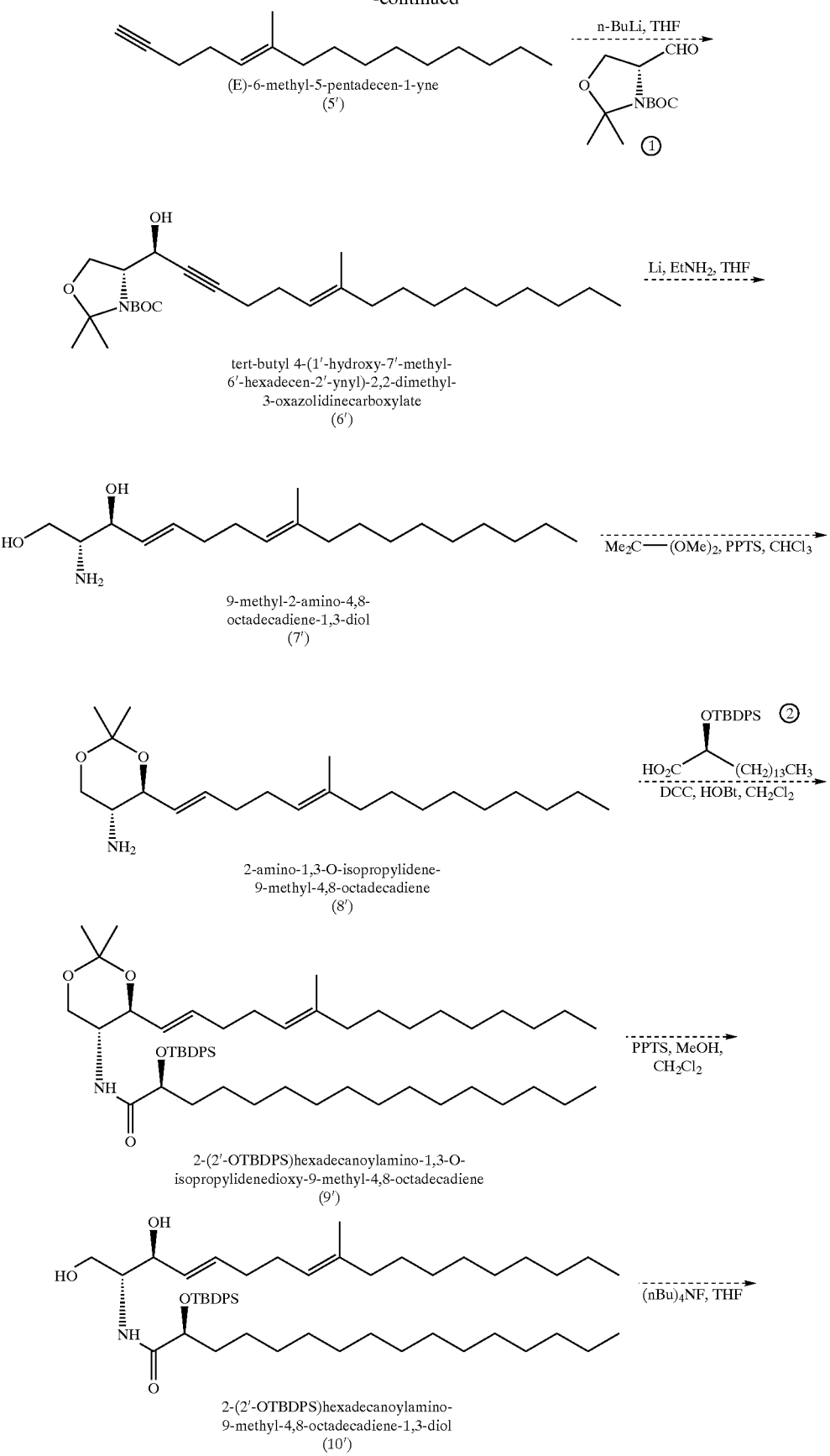

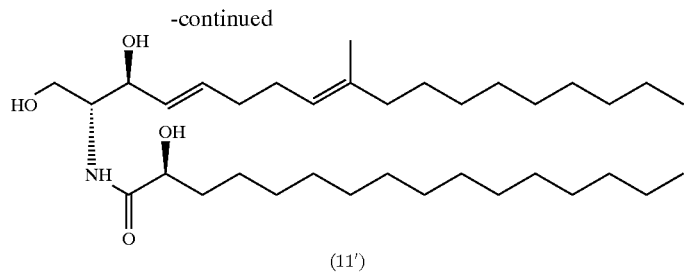

(11')

(A) Synthesis of Starting Materials

2-Undecanone (methyl nonyl ketone) (1') (73.9 g, 434 mmols) and methyl (diethylphosphono)acetate (99.4 g, 433 mmols) were dissolved in dry benzene (300 ml). The solution was stirred at room temperature, and a 28% sodium methoxide solution (83.7 g) in methanol was slowly added. Stirring was continued overnight at room temperature. The reaction mixture was poured into ice water, and extracted with diethyl ether. The organic layer was washed (water and a saturated aqueous solution of sodium chloride), and dried (sodium sulfate), followed by removing the solvent in a vacuum to obtain methyl 3-methyl-2-dodecenoate (2') as a geometric isomer mixture.

A dry THF solution (150 ml) of the crude product, methyl 3-methyl-2-dodecenoate (2') (E/Z mixture, 98.5 g, 0.435 mol), was added dropwise at room temperature to a stirred suspension of LiAlH$_4$ (16.5 g, 0.435 mol) in dry THF (300 ml). The reaction mixture was heated for 2 hours under reflux. After the mixture was reverted to room temperature, water and 10% sulfuric acid were slowly added in sequence, and the resulting mixture was extracted with diethyl ether. The organic layer was washed with water and a saturated aqueous solution of sodium chloride, dried over magnesium sulfate, and then concentrated under vacuum to obtain crude (E)-3-methyl-2-dodecen-1-ol (85.5 g, 99%) as an E/Z mixture. The E/Z ratio of the crude alcohol mixture was found to be 96:4 as a result of 250 MHz $^1$H-NMR analysis. A portion (50 g) of the residue was subjected to silica gel column chromatography (hexane elution) to obtain 41.3 g (83%) of a pure E isomer (3').

An acetonitrile solution (100 ml) of triphenylphosphine (18.6 g, 70.9 mmols) was stirred at 0° C. Bromine (11.4 g, 3.7 ml, 71.3 mmols) was slowly blended into the solution. To the mixture, an acetonitrile (30 ml) solution of (E)-3-methyl-2-dodecen-1-ol (3') was added dropwise, followed by stirring for 2 hours at 0° C. The solvent was removed under vacuum, and the residue was dissolved in dichloromethane. The solution was washed with saturated sodium bicarbonate and a saturated aqueous solution of sodium chloride, then dried over sodium sulfate, and concentrated. Pentane was added to the residue, and a solid formed was removed by filtration. The filtrate was concentrated in a vacuum to obtain 17.9 g (97%) of (E)-1-bromo-3-methyl-2-dodecene (4').

A diethyl ether solution (100 ml) of propargyl bromide (22.4 g, 190 mmols) was added dropwise to magnesium (5.20 g, 210 mmols) and HgCl$_2$ (360 mg, 1.33 mmols) to obtain propargyl magnesium bromide (Grignard reagent). CuCl (200 mg, 2.02 mmols) was added to this Grignard reagent, and the resulting solution was ice-cooled. After a diethyl ether (100 ml) solution of (E)-1-bromo-3-methyl-2-dodecene (4') (18.8 g, 72.0 mmols) was added dropwise, the mixture was stirred for 3 hours at 0° C. The reaction mixture was poured into ice water, acidified with diluted hydrochloric acid, and extracted several times with diethyl ether. The organic layers were combined, and washed with water and a saturated aqueous solution of sodium chloride. A small amount of allene type impurities was removed by silica gel column chromatography (elution with hexane) to obtain pure (E)-6-methyl-5-pentadecen-1-yne (5') (12.7 g, 80%).

(B) Synthesis of the Compound of Example 2

Step 1: An n-hexane solution of n-butyl lithium (1.68 M, 10 ml, 16.8 mmols) was added at −23° C. to a dry THF (50 ml) solution of the (E)-6-methyl-5-pentadecen-1-yne (5') (4.0 g, 18.2 mmols) synthesized in (1)(B). Then, the mixture was stirred for 1 hour at the same temperature under an argon gas. A dry THF (30 ml) solution of the N-Boc-protected (R)-2,2-dimethyl-4-formyloxazolidine (3.7 g, 16.1 mmols) synthesized in (1)(A) was blended at −23° C. into the stirred mixture, and then the resulting mixture was stirred for 3 hours at the same temperature. Subsequently, the reaction mixture was poured into ice water, and extracted several times with diethyl ether. The organic extracts combined were washed (water and a saturated aqueous solution of sodium chloride), dried (magnesium sulfate), and concentrated in a vacuum. The resulting light yellow oily matter was purified by silica gel column chromatography (eluted with hexane:AcOEt=20:1) to obtain 5.17 g (11.5 mmols, 71%) of tert-butyl (4R,1'S)-4-(1'-hydroxy-7'-methyl-6'-hexadecen-2'-ynyl)-2,2-dimethyl-3-oxazolidinecarboxylate (6').

Step 2: A dry THF (100 ml) solution of the tert-butyl (4R,1'S)-4-(1'-hydroxy-7'-methyl-6'-hexadecen-2'-ynyl)-2,2-dimethyl-3-oxazolidinecarboxylate (6') (8.4 g, 18.7 mmols) was added dropwise to an ethylamine (50 g) blue solution of lithium (2 g, 288 mmols) over 1 hour with stirring at −70° C. After stirring was continued for 4 hours at −70° C., the mixture was returned gradually to the ambient temperature, and treated with a saturated ammonium chloride solution. Ethylamine and the solvent were removed in a vacuum, and water was added to the residue. The mixture was extracted several times with diethyl ether. The organic extracts combined were washed with a saturated aqueous solution of sodium chloride, dried over sodium sulfate, and concentrated in a vacuum to obtain 4.5 g (14.4 mmols, 77%) of crude (4E,8E,2R,3S)-9-methyl-2-amino-4,8-octadecadiene-1,3-diol (7') as a brown oil.

Step 3: A mixture of the crude (4E,8E,2R,3S)-9-methyl-2-amino-4,8-octadecadiene-1,3-diol (7') (4.3 g, 13.8 mmols), pyridinium p-toluenesulfonate (PPTS) (3.47 g, 13.8 mmols), and 2,2-dimethoxypropane (20 ml) in trichloromethane (120 ml) was heated for 4 hours under reflux. The mixture was cooled to room temperature, and diluted with trichloromethane. The dilution was washed (a saturated solution of sodium hydrogen carbonate, water, and a saturated aqueous solution of sodium chloride), then dried (sodium sulfate), and concentrated in a vacuum. The residue was purified by silica gel chromatography (eluted with CH$_2$Cl$_2$:MeOH= 50:1) to obtain 4.10 g of (4E,8E,2R,3S)-2-amino-1,3-O-isopropylidene-9-methyl-4,8-octadecadiene (8') as a light brown oil (yield 88% based on the 6' compound). $n_D^{22}$: 1.4751, $[\alpha]_D^{24}$=−8.78 (c=1.85, CHCl$_3$).

The (2S)-2-(tert-butyldiphenylsilyloxy)hexadecanoic acid (2.20 g, 4.10 mmols) synthesized in (1)(B), dicyclohexylcarbodiimide (DCC, 850 mg, 4.1 mmols), and 1-hydroxybenzotriazole (HOBt) (555 mg, 4.10 mmols) were dissolved in dry dichloromethane (40 ml). With the solution being stirred at room temperature, a dry dichloromethane solution (20 ml) of the (4E,8E,2R,3S)-2-amino-1,3-O-isopropylidene-9-methyl-4,8-octadecadiene (8') (1.4 g, 4.1 mmols) was added dropwise. The reaction mixture was stirred for 2 hours at room temperature, and then concentrated in a vacuum to a half amount, and the resulting urea was removed by filtration through Celite. The filtrate was washed (a saturated solution of sodium hydrogen carbonate, water, and a saturated aqueous solution of sodium chloride), dried (magnesium sulfate), and concentrated in a vacuum. The residue was purified by silica gel column chromatography (eluted with hexane:AcOEt,50:1) to obtain 1.82 g (51%) of (4E,8E,2R,3S,2'S)-2-[2'-(OTBDPS) hexadecanoylamino]-1,3-O-(isopropylidenedioxy)-9-methyl-4,8-octadecadiene (9').

Step 4: The (4E,8E,2R,3S,2'S)-2-[2'-(OTBDPS) hexadecanoylamino]-1,3-O-(isopropylidenedioxy)-9-methyl-4,8-octadecadiene (9') (1.1 g, 1.26 mmols) was dissolved in $CH_2Cl_2$:MeOH (1:1, 20 ml). Pyridinium p-toluenesulfonate (PPTS, 320 mg) was added to the solution, the mixture was stirred for 1 hour at room temperature, and the solvent was removed in a vacuum. The residue was dissolved in AcOEt, and then the solution was washed (a saturated solution of sodium hydrogen carbonate, water, and a saturated aqueous solution of sodium chloride), dried (magnesium sulfate), and concentrated in a vacuum. The residue was purified by silica gel column chromatography to obtain (4E,8E,2R,3S,2'S)-2-[2'-(OTBDPS) hexadecanoylamino]-9-methyl-4,8-octadecadiene-1,3-diol (10') (680 mg, 65%).

The TBDPS ether, (4E,8E,2R,3S,2'S)-[2-(2'-(OTBDPS) hexadecanoylamino]-9-methyl-4,8-octadecadiene-1,3-diol (10') (640 mg, 0.71 mmol), was dissolved in THF (50 ml). Tetra-n-butylammonium fluoride (1M THF solution, 1.2 ml, 1.2 mmols) was added to the solution, and the mixture was stirred for 1 hour at room temperature. The reaction mixture was poured into water, and extracted with dichloromethane. The organic layer was washed with water and a saturated aqueous solution of sodium chloride, then dried over magnesium sulfate, and concentrated in a vacuum. The residue was purified by silica gel column chromatography (eluted with hexane:AcOEt, 1:1), and recrystallized from acetone to obtain (4E,8E,2R,3S,2'S)-N-2'-hydroxyhexadecanoyl-9-methyl-4,8-octadecadiene-1,3-diol (11') (424 mg, 93%).

mp: 82.0° C., $[\alpha]^{24}_D$: +8.2 (c=1.0, $CHCl_3$)

Example 3

Synthesis of (4E,2S,3R,2'RS)-N-2'-hydroxyhexadecanoyl-9-methyl-4-octadecene-1,3-diol (1) Preparation of Reaction Materials
(A) Synthesis of N-Boc-Protected (S)-Formyloxazolidine Derivative An N-Boc-protected (S)-2,2-dimethyl-4-formyloxazolidine was synthesized from (S)-serine in accordance with a scheme illustrated below.

(B) Synthesis of a Tert-Butyldiphenylsilyl (TBDPS) Protected Acid (2RS)-2-(tert-butyldiphenylsilyloxy)hexadecanoic acid was synthesized in accordance with a scheme shown below.

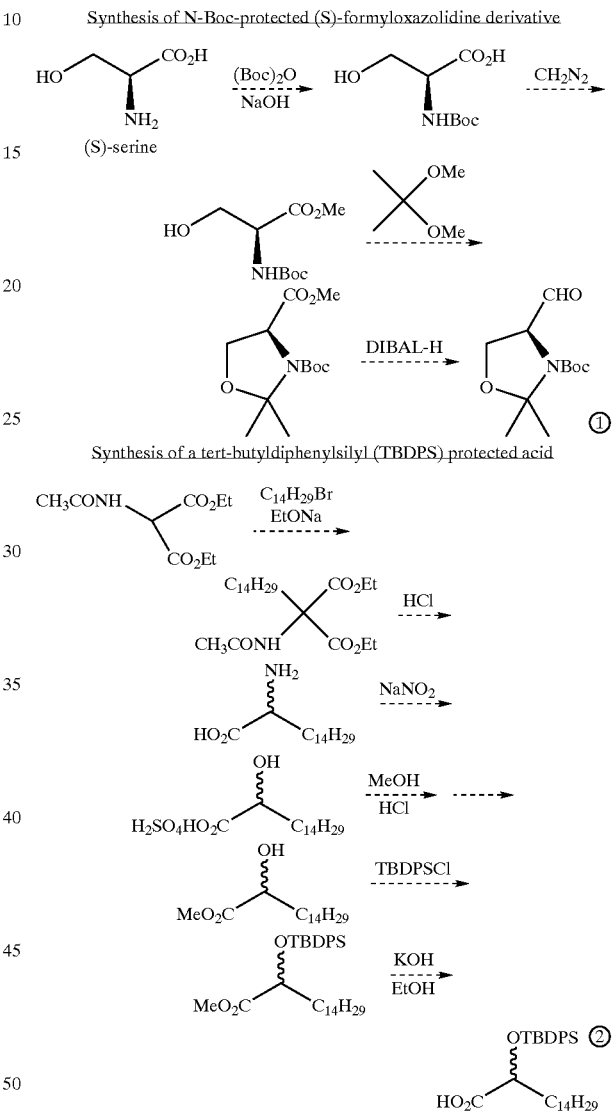

(2) Synthesis of Example 3

A synthesis scheme is shown below.

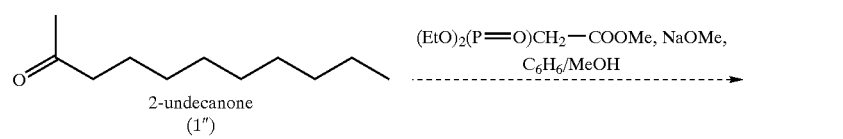

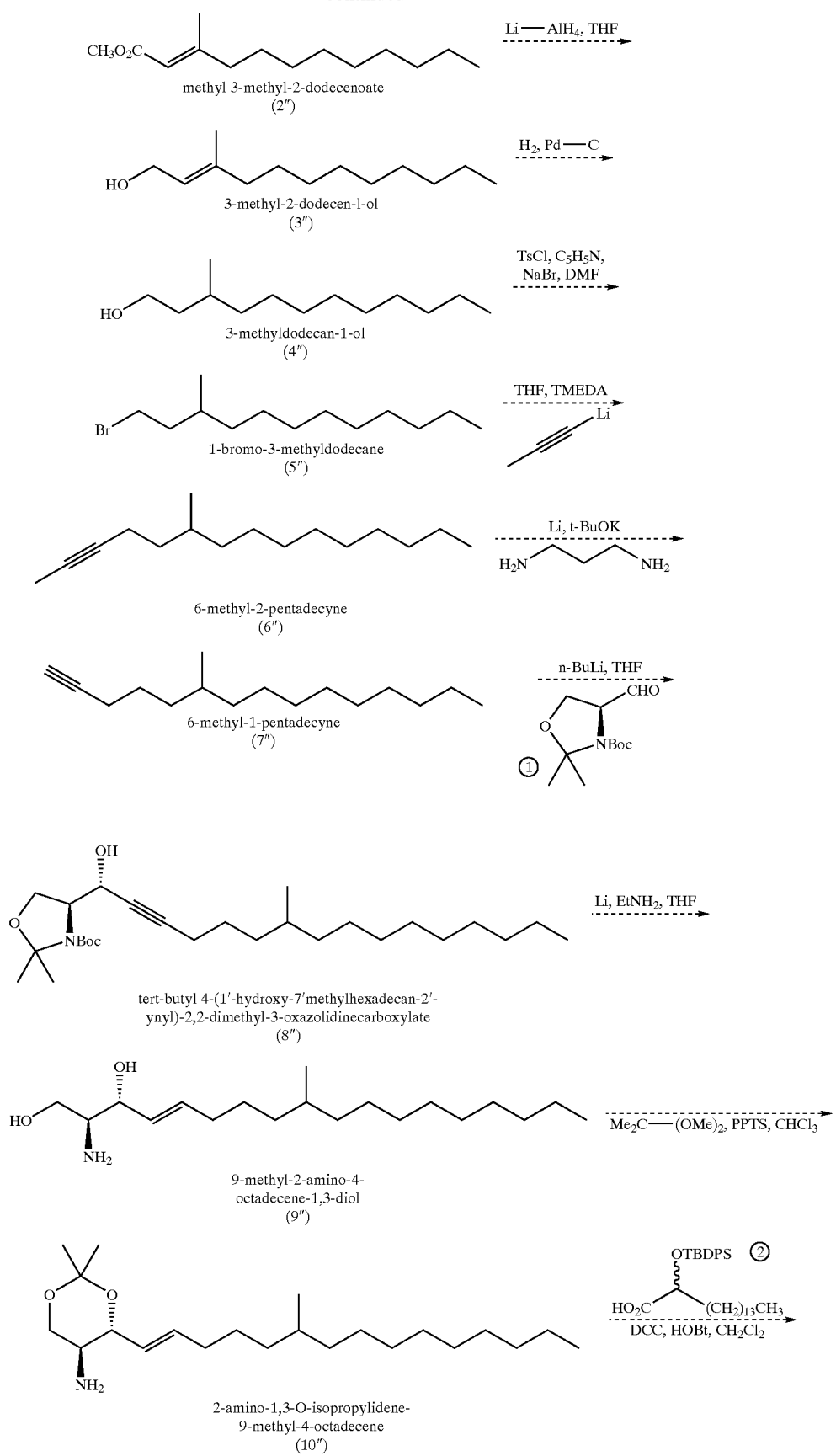

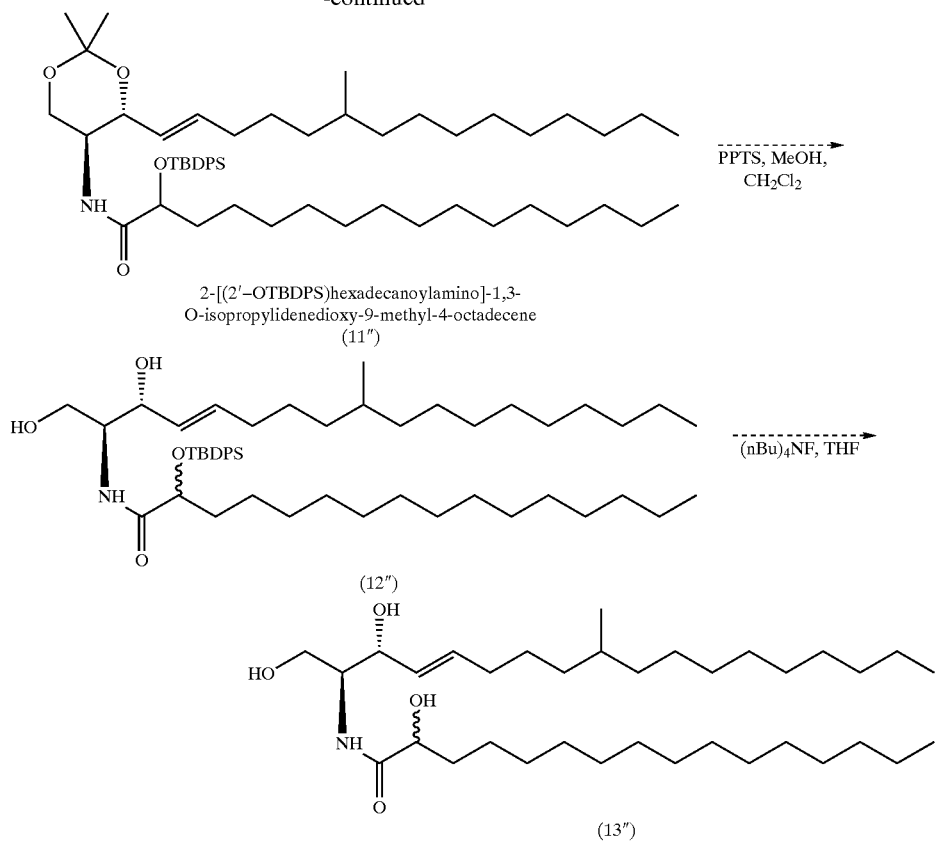

2-[(2'-OTBDPS)hexadecanoylamino]-1,3-
O-isopropylidenedioxy-9-methyl-4-octadecene
(11″)

Step 1: Pd-C (1.0 g) was added to an ethyl acetate solution (300 ml) of 3-methyl-2-dodecen-1-ol (3″) (30 g, 0.15 mol) obtained from 2-undecanone (1″) in the same manner as in Example 2, and the mixture was stirred for 3 days in a hydrogen atmosphere. The reaction mixture was filtered through Celite, and the filtrate obtained was concentrated and then distilled under reduced pressure to obtain 3-methyldodecan-1-ol (4″) (20 g, 67%). b.p. 122–123° C./4 torrs. $^1$H-NMR (90 MHz, CDCl$_3$) 0.8–1.0 (6H,m,Me), 1.0–1.7 (20H,m,2~11-H and OH), 3.66 (2H,q,J=7,1-H).

Step 2: Pyridine (20 ml) was added to a methylene chloride (50 ml) solution of the 3-methyldodecan-1-ol (4″) (12.8 g, 63.9 mols), and p-toluenesulfonyl chloride (12.8 g, 67.1 mmols) was further added under ice-cooling. The reaction mixture was stirred overnight at 4° C., then poured into diluted hydrochloric acid, and extracted with hexane. The organic layer was washed (water, a saturated aqueous solution of sodium bicarbonate, a saturated aqueous solution of sodium chloride), dried (magnesium sulfate), and concentrated under reduced pressure to obtain 21.7 g of a tosylate. Sodium bromide (9.9 g, 96 mols) was added to a DMF solution (100 ml) of the resulting tosylate, and the mixture was stirred overnight at room temperature. The reaction mixture was poured into water, and extracted with hexane. The organic layer was washed (water and a saturated aqueous solution of sodium chloride), dried (magnesium sulfate), and concentrated under reduced pressure to obtain 1-bromo-3-methyldodecane (5″) (15.1 g, 90%). $^1$H-NMR (90 MHz, CDCl$_3$) 0.8–1.0 (6H,m,Me), 1.0–2.0 (19H,m,2~11-H), 3.43 (2H,br t,J=7,1-H).

Step 3: Tetramethylethylenediamine (TMEDA) (15 ml) was added to a THF (80 ml) solution of propyne (about 4 g, 0.1 mol) under argon. To the mixture, n-BuLi (1.55 M, 64.5 ml, 100 mmols) was added dropwise at −78° C. With the temperature being raised gradually to 0° C., the mixture was stirred for 1.5 hours, and then cooled again to −78° C. Thereto, an HMPA-THF (20 ml+20 ml) solution of the 1-bromo-3-methyldodecane (5″) (13.2 g, 50 mmols) was added dropwise, and with the temperature of the mixture being raised gradually to room temperature, stirring was continued overnight. The reaction mixture was poured into a saturated aqueous solution of ammonium chloride, and extracted with hexane. The resulting organic layer was washed (water, a saturated aqueous solution of sodium bicarbonate, a saturated aqueous solution of sodium chloride), dried (magnesium sulfate), and concentrated under reduced pressure. The resulting residue was purified by silica gel column chromatography to obtain 6-methyl-2-pentadecyne (6″) (12.1 g, 97%). $^1$H-NMR (90 MHz, CDCl$_3$) 0.84 (3H,d,J=7,6-Me), 0.88 (3H,t,J=7,15-H), 1.0–1.6 (19H, m,5~14-H), 1.77 (3H,t,J=2.5,1-H), 2.12 (2H,m,4-H).

Step 4: To anhydrous 1,3-diaminopropane (180 ml), which had been distilled, metallic lithium (2.8 g, 0.4 mol) was added under argon stream, and the mixture was stirred for 2 hours at 70° C. After the mixture was allowed to cool, potassium t-butoxide (27 g, 0.24 mol) was added, followed by stirring for 15 minutes. The 6-methyl-2-pentadecyne (6″) (12.1 g, 54.5 mmols) was added dropwise, and the mixture was stirred overnight at room temperature. This reaction was carefully quenched with a saturated aqueous solution of ammonium chloride, and then the mixture was extracted with ether. The resulting organic layer was washed (diluted hydrochloric acid, a saturated aqueous solution of sodium bicarbonate, a saturated aqueous solution of sodium chloride, dried (magnesium sulfate), and concentrated under reduced pressure. The resulting residue was purified by silica gel column chromatography to obtain 6-methyl-1-pentadecyne (7") (9.90 g, 82%). IR and $^1$H-NMR analysis of the product showed the following results: IR (film) 3300 (m,C≡CH), 2130 cm$^{-1}$ (w,C≡C). $^1$H-NMR (90 MHz, CDCl$_3$) 0.84 (3H,d,J=7,6-Me), 0.88 (3H,t,J=7,15-H), 1.0–1.6 (21H,m,4~14-H), 1.93 (1H,t,J=2.5,1-H), 2.0–2.3 (2H,m,3-H).

Step 5: An n-hexane solution (1.68 M, 10 ml, 16.8 mmols) of n-butyl lithium was added at −23° C. to a dry THF solution of the 6-methyl-1-pentadecyne (7") (4.0 g, 18.2 mmols). Then, the mixture was stirred for 1 hour at the same temperature under an argon gas. A dry THF (30 ml) solution of the N-Boc-protected (S)-2,2-dimethyl-4-formyloxazolidine (3.7 g, 16.1 mmols) synthesized in the above (1)(A) was blended at −23° C. into the stirred mixture, and then the resulting mixture was stirred for 3 hours at the same temperature. Subsequently, the reaction mixture was poured into ice water, and extracted several times with diethyl ether. The organic extracts combined were washed (water and a saturated aqueous solution of sodium chloride), dried (magnesium sulfate), and concentrated in a vacuum. The resulting light yellow oily matter was purified by silica gel column chromatography (eluted with hexane:AcOEt= 20:1) to obtain 5.17 g (11.5 mmols, 71%) of tert-butyl (4S,1'R)-4-(1'-hydroxy-7'-methylhexadecan-2'-ynyl)-2,2-dimethyl-3-oxazolidinecarboxylate (8").

Step 6: A dry THF (100 ml) solution of the tert-butyl (4S,1'R)-4-(1'-hydroxy-7'-methylhexadecan-2'-ynyl)-2,2-dimethyl-3-oxazolidinecarboxylate (8") (8.4 g, 18.7 mmols) was added dropwise to an ethylamine (50 g) blue solution of lithium (2 g, 288 mmols) over 1 hour with stirring at −70° C. After stirring was continued for 4 hours at −70° C., the mixture was returned gradually to the ambient temperature, and treated with a saturated ammonium chloride solution. Ethylamine and the solvent were removed in a vacuum, and water was added to the residue. The mixture was extracted several times with diethyl ether. The organic extracts combined were washed with a saturated aqueous solution of sodium chloride, dried over sodium sulfate, and concentrated in a vacuum to obtain 4.5 g (14.4 mmols, 77%) of crude (4E,2S,3R)-9-methyl-2-amino-4-octadecene-1,3-diol (9") as a brown oil.

Step 7: A mixture of the crude (4E,2S,3R)-9-methyl-2-amino-4-octadecene-1,3-diol (9") (4.3 g, 13.8 mmols), pyridinium p-toluenesulfonate (PPTS) (3.47 g, 13.8 mmols), and 2,2-dimethoxypropane (20 ml) in trichloromethane (120 ml) was heated for 4 hours under reflux. The mixture was cooled to room temperature, and diluted with trichloromethane. The dilution was washed (a saturated solution of sodium hydrogen carbonate, water, and a saturated aqueous solution of sodium chloride), then dried (sodium sulfate), and concentrated in a vacuum. The residue was purified by silica gel chromatography (CH$_2$Cl$_2$:MeOH=50:1) to obtain 4.10 g of (4E,2S,3R)-2-amino-1,3-O-isopropylidene-9-methyl-4-octadecene (10") as a light brown oil (yield 88% based on the 8" compound).

The (2RS)-2-(tert-butyldiphenylsilyloxy)hexadecanoic acid synthesized in (1)(B) (2.20 g, 4.10 mmols), dicyclohexylcarbodiimide (DCC, 850 mg, 4.1 mmols), and 1-hydroxybenzotriazole (HOBt) (555 mg, 4.10 mmols) were dissolved in dry dichloromethane (40 ml). With the solution being stirred at room temperature, a dry dichloromethane solution (20 ml) of the (4E,2S,3R)-2-amino-1,3-O-isopropylidene-9-methyl-4-octadecene (10") (1.4 g, 4.1 mmols) was added dropwise. The reaction mixture was stirred for 2 hours at room temperature, and then concentrated in a vacuum to a half amount, and the resulting urea was removed by filtration through Celite. The filtrate was washed (a saturated solution of sodium hydrogen carbonate, water, and a saturated aqueous solution of sodium chloride), dried (magnesium sulfate), and concentrated in a vacuum. The residue was purified by silica gel column chromatography (eluted with hexane:AcOEt,50:1) to obtain 1.82 g (51%) of (4E,2S,3R,2'RS)-2-[2'-(OTBDPS) hexadecanoylamino]-1,3-O-(isopropylidenedioxy)-9-methyl-4-octadecene (11").

Step 8: The (4E,2S,3R,2'RS)-2-[2'-(OTBDPS) hexadecanoylamino]-1,3-O-(isopropylidenedioxy)-9-methyl-4-octadecene (11") (1.1 g, 1.26 mmols) was dissolved in CH$_2$Cl$_2$:MeOH (1:1, 20 ml). Pyridinium p-toluenesulfonate (PPTS, 320 mg) was added to the solution, the mixture was stirred for 1 hour at room temperature, and the solvent was removed in a vacuum. The residue was dissolved in AcOEt, then the solution was washed (saturated sodium hydrogen carbonate, water, and a saturated aqueous solution of sodium chloride), dried (magnesium sulfate), and concentrated in a vacuum. The residue was purified by silica gel column chromatography to obtain (4E,2S,3R,2'RS)-2-[2'-(OTBDPS) hexadecanoylamino]-9-methyl-4-octadecene-1,3-diol (12") (680 mg, 65%).

The TBDPS ether, (4E,2S,3R,2'RS)-2-[2'-(OTBDPS) hexadecanoylamino]-9-methyl-4-octadecene-1,3-diol (640 mg, 0.71 mmol), was dissolved in THF (50 ml). Tetra-n-butylammonium fluoride (1M THF solution, 1.2 ml, 1.2 mmols) was added to the solution, and the mixture was stirred for 1 hour at room temperature. The reaction mixture was poured into water, and extracted with dichloromethane. The organic layer was washed (water and a saturated aqueous solution of sodium chloride), then dried (magnesium sulfate), and concentrated in a vacuum. The residue was purified by silica gel column chromatography (hexane:AcOEt, 1:1), and recrystallized from acetone to obtain (4E,2S,3R,2'RS)-N-2'-hydroxyhexadecanoyl-9-methyl-4-octadecene-1,3-diol (13") (400 mg, 89%). mp: 52–57° C., $[\alpha]^{20}_D$: +3.7 (c=0.06, CHCl$_3$)

Example 4

Edg Receptor Response Test

HL 60 cells were obtained from a cell bank, and subcultured for about 50 passages over a half-year period in accordance with the method described in BBRC '98, 263, p. 253 using an RPMI-1640 culture medium (Gibco) containing 10% fetal bovine serum to prepare a premyeloblastoma cell strain HL60 expressing Edg receptors on the cell surface. Using the premyeloblastoma cell strain HL60 expressing Edg receptors on the cell surface, the cell response of test substances was investigated. An increase in the intracellular Ca$^{2+}$ concentration was measured as an indicator of cell response. It is reported that when the Edg receptor on the HL60 cell surface is bound to AHOP, it phosphorylates G protein to activate IP$_3$ kinase, whereafter the intracellular Ca$^{2+}$ concentration increases (FEBS Letter '96, 379, p. 260, BBRC '98, 253, p. 253). Thus, the intracellular Ca$^{2+}$ concentration serves as an indicator of Edg receptor response.

A Ca$^{2+}$ chelating reagent, Fura-2AM, was taken into HL60 cells.

A cell suspension (1.2 ml) was charged into a quartz cell, which was then mounted on a fluorometer LS50B (Perkin Elmer, for cell measurement). An excitation wavelength was alternately switched between 340 nm (exciting Fura-2 having chelated Ca$^{2+}$) and 380 nm (exciting unreacted Fura-2)

at intervals of 0.5 milli second, and fluorescence intensity at 510 nm was measured.

Each test substance was added at an end concentration of 30 μM by means of a microsyringe, and then fluorescence intensity was traced to investigate whether $Ca^{2+}$ would increase or not. It was also confirmed whether $Ca^{2+}$ would increase or not when AHOP (1 μM) was added after addition of the test substance. Through these tests, the AHOP antagonism of each substance was studied.

After the compound of Example 2 or the compound of Example 3 was added, the increase in the intracellular $Ca^{2+}$ concentration by the addition of AHOP was inhibited. This finding suggested the possibility that these two substances were Edg antagonistic.

Then, a study was made of the dose dependency of the intracellular $Ca^{2+}$ increase inhibiting action of the two substances suggested to have antagonism, the compound of Example 2 and the compound of Example 3. Suramin, already confirmed to have antagonistic action, was used as a comparison. The experimental procedure was the same as described above, except that AHOP (1 μM) was added after addition of the test substance at varying concentration. An increase in the $Ca^{2+}$ concentration was evaluated by an increased $Ca^{2+}$ concentration (%) as a value relative to the increased $Ca^{2+}$ concentration in a negative control group (no drug added).

As a result, the compound of Example 3 at a concentration of 0.3 to 3 μM, and the compound of Example 2 at a concentration of 0.03 to 0.3 μM, dose-dependently suppressed the $Ca^{2+}$ concentration increase by AHOP. The results are shown in FIG. 1.

A 50% inhibitory concentration ($ED_{50}$) for the intracellular $Ca^{2+}$ concentration increase was 1.2±0.1 μM for the compound of Example 3, and 0.041±0.1 μM for the compound of Example 2. The $ED_{50}$ of suramin, whose Edg antagonism was already reported, is 1.8±0.1 μM. In comparison, the strength of the action that the compound of Example 2 has is about 40 times as high. These $ED_{50}$ values are shown in Table 1.

TABLE 1

| 50% Inhibition Point for $Ca^{2+}$ Increase | | |
|---|---|---|
| | Substance | $ED_{50}$ (μM) |
| Positive control | suramin | 1.8 ± 0.1 |
| Test substance | Example 2 | 0.041 ± 0.1 |
| | Example 3 | 1.2 ± 0.1 |

Example 5

Competition Experiments Using $^3$H-AHOP

The same premyeloblastoma cell strain HL60 expressing Edg receptors on the cell surface as used in Example 4 was used. The cells were harvested by centrifugation, then suspended in an F-12 culture medium (stored at 4° C., 10 ml), and carried into an RI laboratory. $^3$H-AHOP (15 μCi/1 nM) at an end concentration of 1 nM, and an unlabeled compound (the compound of Example 2 or Example 3) at an end concentration of 10 nM, 30 nM or 100 nM were each added to 200 μl of the cell suspension (1×10$^6$ cells/ml F-12), and a binding test was conducted for 30 minutes at 4° C. (with occasional stirring). After centrifugation for 7 minutes at 12,000 rpm, the supernatant was rapidly (without damaging cell pellets) discarded with a micropipetter. The cell pellets were suspended in 1.5 ml of Ready Safe (Beckman), whereafter the suspension was transferred into a vial and measured for radioactivity by a liquid scintillation counter L2100 (Beckman).

As a result, the compounds of Example 2 and Example 3 were competitive with $^3$H-AHOP, as with AHOP. Thus, these two substances were considered to bind to Edg specifically.

The compounds of Example 2 and Example 3 were subjected to the same competition experiments as described above, except that they were added at concentrations of 1 nM, 3 nM and 10 nM. Dose-dependent inhibition of binding of $^3$H-AHOP (to HL60 cells) was observed. The results are shown in FIG. 2.

Example 6

Action on Vascular Smooth Muscle

The action of the test substances on vascular smooth muscle growth was investigated.

It is hypothesized that with the progression of arteriosclerosis, vascular smooth muscle cells are transformed from the contractile type to the synthetic type, and while secreting inflammatory cytokines, the vascular smooth muscle cells proliferate, causing arteriosclerotic lesions to proceed (Roth's hypothesis). There is a report that Edg receptors are expressed on the surface of vascular smooth muscle cells (The American Society for Pharmacology and Experimental Therapeutics '00, Vol. 58, p. 449; Vascular smooth muscle cells are reported to proliferate in response to sphingosylphosphorylcholine which acts on Edg receptors like AHOP (The American Physiological Society '98, C1255)).

Thus, the actions of the compounds of Examples 2 and 3 on the growth of vascular smooth muscle cells were measured in the manner described below. Suramin confirmed to have Edg receptor antagonism was used as a positive control.

The rat carotid intima was rubbed by ballooning, and a tissue fragment was cultured by explant culture. Two weeks later, vascular smooth muscle cells harvested were cultured in a DMEM culture medium (Gibco) containing 10% fetal bovine serum. The cultures were subcultured several times for stabilization, whereafter the subcultures were seeded at a cell density of 5×10$^3$ cells/cm$^2$ for use in experiments.

Along with the growth factor sphingosylphosphorylcholine (10 μM), the compound of Example 2 or 3, or suramin was added to the cells, and 24 hours later, the cell density was measured by BrdU assay (Science '82, 218, p. 474, Cytometry '85, 6, p. 584).

As a result, the compounds of Examples 2 and 3 inhibited vascular smooth muscle growth dose-dependently at concentrations of 0.3 to 3 μM and 1 to 10 μM, respectively. Suramin, used as the positive control, inhibited vascular smooth muscle growth at concentrations of 30 and 100 μM. The results are shown in FIG. 3.

Example 7

Anti-Inflammatory Tests Using Pseudo-Blood Vessel Model

At the site of injury in vivo, the exposed collagen (extracellular matrix) is targeted as an injury signal, and platelets are aggregated there. Inflammatory cytokines (such as PDGF) released from the aggregated and activated plate lets advance inflammation. Moreover, severe inflammation is presumed to destroy homeostasis of cardiovascular organs and progress arteriosclerosis. AHOP is also considered to have the same action as PDGF.

Hence, AHOP was used as an inflammation-inducing agent to establish a pseudo-blood vessel in vitro model. Using the model, it was studied whether the compounds of the present invention show anti-inflammatory action, and thereby have possibilities for maintaining the homeostasis of cardiovascular organs and acting in a direction toward improvement of pathophysiological states.

(1) Inflammation-Inducing Action of AHOP in Pseudo-Blood Vessel Model

Transwells were used, each consisting of an upper compartment separated from a lower compartment by a porous membrane. A single layer of bovine endothelial cells was cultured on the porous membrane at the bottom surface of the transwell upper compartment. A suspension of fluorescence-labeled neutrophils was added to the transwell upper compartment, and AHOP was suspended within the lower compartment to an end concentration of 0.1 to 10 microM. That is, a pseudo-blood vessel in vitro inflammation model was thus constructed in which the upper compartment and the lower compartment of the transwell were isolated from each other via the endothelial layer, and the upper compartment corresponded to the interior of a blood vessel, while the lower compartment corresponded to the site of inflammation outside the blood vessel. Measurements were made of the number of the neutrophils passing from the upper compartment into the lower compartment through the endothelial layer, and the number of the neutrophils adhering to the endothelial layer. At an AHOP concentration of 10 microM, the transmigration through the endothelial layer and the adhesion of the neutrophils were promoted significantly. That is, AHOP was considered to act as an inflammation-inducing substance.

(2) Action of the Compounds (Edg antagonists) of the Present Invention on Inflammatory Cell-Vascular Endothelial Cell Interaction AHOP was used as an inflammation inducer, and the effect of the compounds of Examples 2 and 3, showing Edg antagonism, on the pseudo-blood vessel in vitro inflammation model was investigated.

That is, the compound of Example 2 or 3 was added in an amount of 0.01 to 1 microM to the upper compartment or lower compartment of the transwell, and 10 microM AHOP was placed in the lower compartment to induce inflammation. As a control, inflammation was induced in the same way as above but without addition of any compounds of the invention.

Measurements were made of the number of the neutrophils passing from the upper compartment into the lower compartment through the endothelial layer, and the number of the neutrophils adhering to the endothelial layer. A relative neutrophil count (%) was calculated from the following equation:

Relative neutrophil count (%)=[number of neutrophils (passing and adhering) in the experimental group]/[number of neutrophils (passing and adhering) in the control]×100

The results are shown in FIG. 4. As shown in the drawing, neutrophil transmigration and adhesion were suppressed by 0.1 and 1 microM of the compounds of Examples 2 and 3.

Hence, when AHOP is used as an inflammation-inducing agent in the pseudo-blood vessel in vitro model, the compounds of Examples 2 and 3 are assumed to exert anti-inflammatory action, and thereby have possibilities for maintaining the homeostasis of cardiovascular organs and acting in a direction toward improvement of pathophysiological states.

Example 8

Ligation-Associated Myocardial Infarction Model

The compound of Example 2 was used as a test substance for investigating its effect on myocardial infarction due to reperfusion following ligation of the rabbit coronary artery.

Male NZW rabbits (weighing 2.83 to 3.20 kg) were purchased from Kitayama Labes, Co. Ltd., and bred and raised under the conditions: room temperature 20–26° C., humidity 40–70%, and illumination time 12 hours/day (7-19:00). The animals were allowed food and water ad libitum, and quarantined and acclimatized for 2 weeks or more. Then, the animals in good health were used.

The above rabbits were administered 10 mg/kg of the compound of Example 2 through the jugular vein under anesthesia, and then the compound of Example 2 was continuously infused in a dose of 6.9 micro g/kg/min. In a control group, physiological saline (hereinafter referred to as PS) was administered in the same manner as in the experimental group. Then, coronary artery was ligated for 30 minutes, whereafter the ligature was released for reperfusion, and the blood pressure in the carotid artery, the pulse rate and the number of arrhythmias were measured. The carotid arterial blood pressure and pulse rate were measured before administration, during continuous intravenous infusion, during the ligation period (15 minute later and 30 minutes later), and during reperfusion. The carotid arterial blood pressure was calculated as mean blood pressure. The number of arrhythmias was counted as the number of extrasystoles that appeared during the ligation period (for 30 minutes) or during reperfusion. The results are shown in Tables 2 and 3.

After 3 hours of reperfusion, the heart was removed, and sliced into 6 pieces. The living tissues were stained with 2,3,5-triphenyltetrazolium hydrochloride (TTC), the area of the infarct due to ligation was measured, and the percent of the infarct with respect to the area of the left ventricle was calculated. The results are shown in Table 4.

TABLE 2

Effects of the compound of Example 2 on blood pressure and pulse rate

| Item | Drug | No. of animals | Before administration | Continued i.v. infusion | Ligation (min) 15 | Ligation (min) 30 | Reperfusion (min) 180 |
|---|---|---|---|---|---|---|---|
| Mean blood pressure | PS | 4 | 74 ± 3 | 75 ± 4 | 54 ± 8 | 64 ± 4 | 68 ± 3 |
| | Ex. 2 | 4 | 83 ± 4 | 74 ± 9 | 59 ± 10 | 66 ± 8 | 68 ± 4 |

TABLE 2-continued

Effects of the compound of Example 2 on blood pressure and pulse rate

| Item | Drug | No. of animals | Before administration | Continued i.v. infusion | Ligation (min) 15 | Ligation (min) 30 | Reperfusion (min) 180 |
|---|---|---|---|---|---|---|---|
| (mmHg) Pulse rate (beats/min) | PS | 4 | 299 ± 12 | 293 ± 10 | 255 ± 24 | 269 ± 18 | 269 ± 14 |
| | Ex. 2 | 4 | 301 ± 9 | 283 ± 10 | 270 ± 9 | 282 ± 4 | 256 ± 10 |

TABLE 3

Effect of the compound of Example 2 on the number of arrhythmias

| Drug | No. of animals | Ligation | Reperfusion |
|---|---|---|---|
| PS | 4 | 22 ± 10 | 19 ± 12 |
| Ex. 2 | 4 | 12 ± 5 | 17 ± 6 |

TABLE 4

Effect of the compound of Example 2 on the percent area of the infarct

| Drug | No. of animals | Infarct/left ventricle (%) |
|---|---|---|
| PS | 4 | 17.9 ± 2.4 |
| Ex. 2 | 4 | 14.0 ± 2.1 |

The compound of Example 2 tended to inhibit the ligation-associated decrease in pulse rate and reduce the number of arrhythmias due to ligation in rabbit acute myocardial infarction models. The compound of Example 2 also showed a tendency toward decreasing the percent area of the infarct.

INDUSTRIAL APPLICABILITY

The compounds of the present invention show an excellent Edg receptor antagonizing action. Pharmaceuticals comprising the compounds of the present invention as an active ingredient exert excellent therapeutic effects on cardiovascular diseases (e.g. arteriosclerosis, cardiac diseases), cancer, rheumatism, diabetic retinopathy, and respiratory diseases.

What is claimed is:

1. An aliphatic compound represented by the following formula (I) or pharmacologically acceptable salts thereof:

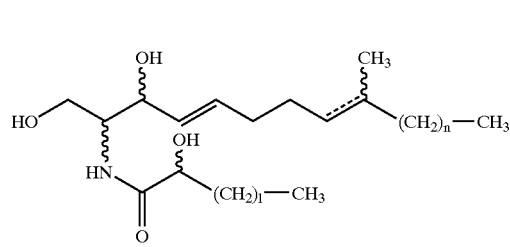

(I)

where n denotes an integer of 1 to 11, and l denotes an integer of 1 to 16,
said aliphatic compound being an optical isomer of a (2R, 3S,2'S) configuration when an 8-position thereof is a double bond, or an optical isomer of a (2S,3R,2'RS) configuration when the 8-position is a single bond.

2. The compound represented by the formula (I) or pharmacologically acceptable salts thereof according to claim 1, said compound being a compound of the following formula (II):

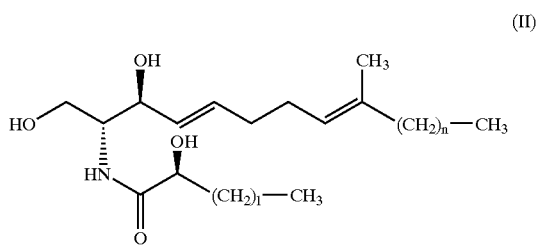

(II)

where l and n are as defined in claim 1.

3. The compound represented by the formula (I) or pharmacologically acceptable salts thereof according to claim 1, said compound being a compound of the following formula (III):

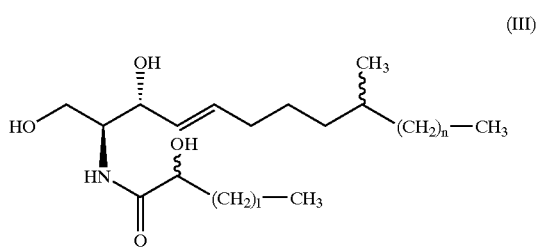

(III)

where l and n are as defined in claim 1.

4. The compound represented by the formula (I) or pharmacologically acceptable salts thereof according to claim 1, said compound being a compound of the following formula (IV):

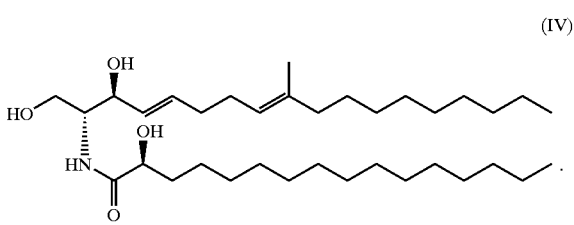

(IV)

5. The compound represented by the formula (I) or pharmacologically acceptable salts thereof according to claim 1, said compound being a compound of the following formula (V):

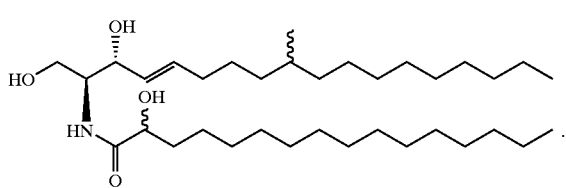

(V)

6. A method for producing the compound of the formula (I) according to claim 1, comprising the steps of:
   (1) reacting an alkenylalane in (E)-form of the following formula:

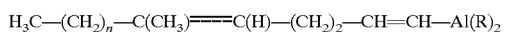

H$_3$C—(CH$_2$)$_n$—C(CH$_3$)═══C(H)—(CH$_2$)$_2$—CH═CH—Al(R)$_2$ where n is as defined in claim 1, and R denotes an alkyl group, with an oxazoline aldehyde derivative of the following formula, having the same optical isomerism as the 2-position of the desired compound:

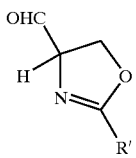

where R' represents an alkyl group or an aryl group;

(2) ring-opening the oxazoline produced in the step (1) to obtain a compound having an NH$_2$ group and an —OC(═O)R' group; and
   (3) N-acylating the product of the step (2) with an acylating agent having the same optical isomerism as the 2'-position of the desired compound, and then eliminating a —C(═O)R' group.

7. A method for producing the compound according to claim 2, comprising the steps of:
   (1) reacting of HC≡C—(CH$_2$)$_2$—CH═C(CH$_3$)—(CH$_2$)$_n$CH$_3$ in (E)-form (where n is as defined in claim 2) with an N-protected (R)-formyloxazolidine derivative of the following formula:

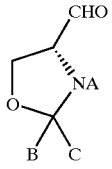

where A is a protective group for N, and B and C each represent an alkyl group;
   (2) converting the triple bond of the product of the step (1) into an (E)-form double bond, and simultaneously deprotecting the oxazolidine at it undergoes ring-opening, thereby obtaining a compound having an NH$_2$ group and an OH group;
   (3) protecting the hydroxyl group of the product of the step (2), and reacting the protected compound with a compound of the following formula:

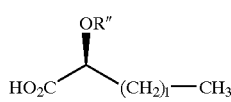

where R" is a protective group for OH, and l is as defined in claim 2; and
   (4) deprotecting the hydroxyl group and eliminating the R" group.

8. A method for producing the compound according to claim 3, comprising the steps of:
   (1) saturating an unsaturated moiety of HO—CH$_2$—CH═C(CH$_3$)—(CH$_2$)$_n$CH$_3$ (where n is as defined in claim 3) by catalytic reduction;
   (2) substituting a hydroxyl group of the product of the step (1) by bromine;
   (3) substituting the bromine of the product of the step (2) by CH$_3$—C≡C—;
   (4) shifting the position of a triple bond of the product of the step (3) to a terminal thereof to obtain a compound terminated with the triple bond;
   (5) reacting said compound terminated with the triple bond with an N-protected (S)-formyloxazolidine derivative of the following formula:

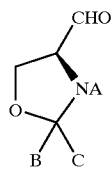

where A is a protective group for N, and B and C each represent an alkyl group;
   (6) converting the triple bond of the product of the step (5) into an (E)-form double bond, and simultaneously deprotecting the oxazolidine as it undergoes ring-opening, thereby obtaining a compound having an NH$_2$ group and an OH group;
   (7) protecting the hydroxyl group of the product of the step (6), and reacting the protected compound with a compound of the following formula:

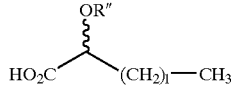

where R" is a protective group for OH, and l is as defined in claim 3; and
   (8) removing the protective group for the hydroxyl group and eliminating the R" group.

9. A pharmaceutical antagonizing endothelial differentiation gene (Edg) receptor, said pharmaceutical comprising the compound or pharmacologically acceptable salts thereof according to any one of claims 1 to 5 as an active ingredient.

10. The pharmaceutical according to claim 9 for treatment of cardiovascular disease.

11. The pharmaceutical according to claim 10, wherein the cardiovascular disease is arteriosclerosis.

12. The pharmaceutical according to claim 9 for treatment of cancer.

13. The pharmaceutical according to claim 9 for treatment of rheumatism.

14. The pharmaceutical according to claim 9 for treatment of diabetic retinopathy.

15. The pharmaceutical according to claim 9 for treatment of respiratory disease.

16. The pharmaceutical according to claim 10, wherein the cardiovascular disease is cardiac disease.

* * * * *